US010174006B2

(12) United States Patent
Ghosh et al.

(10) Patent No.: US 10,174,006 B2
(45) Date of Patent: Jan. 8, 2019

(54) TOPICAL AQUEOUS OPHTHALMIC COMPOSITIONS CONTAINING A 1H-INDOLE-1-CARBOXAMIDE DERIVATIVE AND USE THEREOF FOR TREATMENT OF OPHTHALMIC DISEASE

(71) Applicant: Novartis AG, Basel (CH)

(72) Inventors: Malay Ghosh, Fort Worth, TX (US); Christopher Michael Adams, Somerville, MA (US); Stephanie Kay Dodd, Ayer, MA (US); Stephen Hedrick Poor, Winthrop, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/292,082

(22) Filed: May 30, 2014

(65) Prior Publication Data

US 2014/0364392 A1 Dec. 11, 2014

Related U.S. Application Data

(60) Provisional application No. 61/831,834, filed on Jun. 6, 2013.

(51) Int. Cl.
| | | |
|---|---|---|
| A61K 31/55 | (2006.01) | |
| A61K 31/519 | (2006.01) | |
| A61K 31/506 | (2006.01) | |
| A61K 31/4439 | (2006.01) | |
| A61K 31/724 | (2006.01) | |
| C07D 403/12 | (2006.01) | |
| C07D 401/12 | (2006.01) | |
| C07D 403/14 | (2006.01) | |
| C07D 413/14 | (2006.01) | |
| C07D 471/04 | (2006.01) | |
| C07D 487/04 | (2006.01) | |
| C07D 495/04 | (2006.01) | |
| C07D 519/00 | (2006.01) | |
| A61K 9/00 | (2006.01) | |
| A61K 47/02 | (2006.01) | |
| A61K 47/10 | (2017.01) | |
| A61K 47/18 | (2017.01) | |
| A61K 47/26 | (2006.01) | |
| A61K 47/32 | (2006.01) | |
| A61K 47/34 | (2017.01) | |
| A61K 9/08 | (2006.01) | |
| A61K 47/38 | (2006.01) | |

(52) U.S. Cl.
CPC .......... *C07D 403/12* (2013.01); *A61K 9/0048* (2013.01); *A61K 9/08* (2013.01); *A61K 31/4439* (2013.01); *A61K 31/506* (2013.01); *A61K 31/519* (2013.01); *A61K 31/55* (2013.01); *A61K 31/724* (2013.01); *A61K 47/02* (2013.01); *A61K 47/10* (2013.01); *A61K 47/186* (2013.01); *A61K 47/26* (2013.01); *A61K 47/32* (2013.01); *A61K 47/34* (2013.01); *A61K 47/38* (2013.01); *C07D 401/12* (2013.01); *C07D 403/14* (2013.01); *C07D 413/14* (2013.01); *C07D 471/04* (2013.01); *C07D 487/04* (2013.01); *C07D 495/04* (2013.01); *C07D 519/00* (2013.01)

(58) Field of Classification Search
CPC .. A61K 31/4439; A61K 31/55; A61K 31/519; A61K 31/506; A61K 9/004847; A61K 9/02; A61K 9/20; A61K 9/186; A61K 9/26; A61K 9/32; A61K 9/34; A61K 9/38; A61K 9/08; C07D 495/04; C07D 487/04; C07D 471/04; C07D 413/14; C07D 403/14; C07D 519/00; C07D 401/12
USPC ............ 514/58, 215, 264.1, 265.1, 269, 339
See application file for complete search history.

(56) References Cited

U.S. PATENT DOCUMENTS

| | | | |
|---|---|---|---|
| 3,931,319 A | 1/1976 | Green et al. | |
| 4,027,020 A | 5/1977 | Green et al. | |
| 4,407,791 A | 10/1983 | Stark | |
| 4,525,346 A | 6/1985 | Stark | |
| 4,836,986 A | 6/1989 | Ogunbiyi et al. | |
| 5,037,647 A | 8/1991 | Chowhan et al. | |
| 5,300,287 A | 4/1994 | Park | |
| 5,362,758 A * | 11/1994 | Ahmed ................ | A61K 9/0048 424/427 |
| 5,800,807 A * | 9/1998 | Hu ....................... | A61K 9/0048 424/78.04 |

(Continued)

FOREIGN PATENT DOCUMENTS

| | | |
|---|---|---|
| JP | 11-512445 A | 10/1999 |
| JP | 2002-509101 | 3/2002 |

(Continued)

OTHER PUBLICATIONS

Boddu, et al., "Drug Delivery to the Back of the Eye Following Topical Administration: An Update on Research and Patenting Activity", Recent Patents on Drug Delivery & Formulation, Apr. 1, 2014 (Apr. 1, 2014), pp. 27-36, vol. 8, No. 1, Bentham Science Publishers.

(Continued)

*Primary Examiner* — Ganapathy Krishnan
(74) *Attorney, Agent, or Firm* — Asha K. Nadipuram

(57) ABSTRACT

The present invention is directed to the provision of a multi-dose topical ophthalmic composition containing a 1H-indole-1-carboxamide and use thereof for treatment of ophthalmic disease. More specifically the present invention is directed to a multi-dose aqueous ophthalmic composition (e.g., a solution, a suspension, an emulsion or the like) containing a 1H-indole-1-carboxamide (e.g., N-(1-methyl-5-(trifluoromethyl)-1H-pyrazol-3-yl)-5-((6-((methylamino) methyl)pyrimidin-4-yl)oxy)-1H-indole-1-carboxamide) and use thereof for treatment of an ophthalmic disease at the back of the eye such as age related macular degeneration (AMD).

18 Claims, 3 Drawing Sheets

(56) References Cited

U.S. PATENT DOCUMENTS

| | | | | |
|---|---|---|---|---|
| 6,468,548 B1* | 10/2002 | Kis | ............... | A61K 9/0048 424/400 |
| 8,242,125 B2* | 8/2012 | Artman, III | ............ | A61K 31/18 514/264.1 |
| 2008/0089953 A1* | 4/2008 | Chowhan | ............ | A61K 31/7034 424/660 |
| 2010/0249062 A1* | 9/2010 | Matsumura | ............ | A61K 9/0048 514/57 |
| 2012/0269862 A1* | 10/2012 | Chowhan | ............ | A61K 9/0048 424/278.1 |

FOREIGN PATENT DOCUMENTS

| WO | 9109523 A1 | 7/1991 | | |
|---|---|---|---|---|
| WO | 1997/10805 A1 | 3/1997 | | |
| WO | 1999/3605 A1 | 7/1999 | | |
| WO | 2010066684 A2 | 6/2010 | | |
| WO | 2010066685 A1 | 6/2010 | | |
| WO | WO 2010/066684 A2 * | 6/2010 | ............ | C07D 403/12 |
| WO | 2012055884 A1 | 5/2012 | | |
| WO | 2014197584 A1 | 12/2014 | | |

OTHER PUBLICATIONS

International Search Authority, International Search Report, PCT/US2014/040892, dated Sep. 26, 2014, pp. 1-7.

International Search Authority, Written Opinion of the International Searching Authority, PCT/US2014/040892, dated Sep. 26, 2014, pp. 1-7.

International Search Authority, International Preliminary Report on patentability, PCT/US2014/040892, dated Dec. 8, 2015, 7 pages.

Mastropietro, David. J. et al.: "Prevalence and trends of cellulosics in pharmaceutical dosage forms", Drug Development and Industrial Pharmacy, Feb. 2013, vol. 39, No. 2, p. 382-392.

* cited by examiner

TOPICAL AQUEOUS OPHTHALMIC COMPOSITIONS CONTAINING A 1H-INDOLE-1-CARBOXAMIDE DERIVATIVE AND USE THEREOF FOR TREATMENT OF OPHTHALMIC DISEASE

TECHNICAL FIELD OF THE INVENTION

The present invention is related to a multi-dose topical ophthalmic composition containing a 1H-indole-1-carboxamide and use thereof for treatment of ophthalmic condition or disease. More specifically the present invention relates to a to multi-dose aqueous ophthalmic composition (e.g., a solution, a suspension, an emulsion or the like) containing a 1H-indole-1-carboxamide (e.g., N-(1-methyl-5-(trifluoromethyl)-1H-pyrazol-3-yl)-5-((6-((methylamino)methyl)pyrimidin-4-yl)oxy)-1H-indole-1-carboxamide) and use thereof for treatment of an ophthalmic condition or disease at the back of the eye such as age related macular degeneration (AMD).

BACKGROUND OF THE INVENTION

Ophthalmic diseases such as AMD, which affect the back of the eye, particularly the retina, choroid and surrounding tissues, are very difficult to treat. Accessibility to the back of eye is one of the main reasons for this difficulty. Currently, most back of the eye or retinal/choroidal diseases are treated using intravitreal injections, which delivers a drug in the vitreous adjacent the retina. In this manner, the back of the eye is exposed to a concentration of the drug that is sufficiently high that the drug can be effective to treat a disease at the back of the eye.

Of course, intravitreal administration of drugs suffers from significant drawbacks. Patients are typically averse to having a needle penetrate into their eyes. Further, such administration of drug usually must be performed by a doctor or other trained individual, which typically requires a patient to make frequent visits to a hospital or other medical establishment to receive such administration. Both of these drawbacks can cause poor patient compliance with drug administration due scheduling problems, human avoidance and the like. Moreover, injection related risks such as endophthalmitis, retinal detachment, cataract, intraocular inflammation and others associated with the administration of intravitreal therapeutics make this route of administration less attractive.

In response to these drawbacks, the ophthalmic pharmaceutical industry has sought to provide sustained release formulations that are still provided by intravitreal administration, but which provide drug over extended periods of time. These formulations can be administered to a patient less often thereby lowering the administration burden on the patient. However, such formulations can suffer from additional risk since larger gauge needles are oftentimes used to introduce the formulations into the eye and those needles can increase multiple of the aforementioned risks associated with standard intravitreal injections.

The ophthalmic pharmaceutical industry has also sought to create drug is delivery devices that can provide sustained release and/or may be refillable. Such devices, like sustained release formulations, can lower the burden of drug administration for the patient and typically avoid the requirement of intravitreal injections. However, application of such devices often requires the performance of relatively invasive surgery and, in the case of refillable devices, the patient is typically still required to visit a hospital or other medical establishment relatively frequently.

In contrast to injections and devices, the ophthalmic pharmaceutical industry has found that topical administration of aqueous compositions is non-invasive and very convenient. However, topical administration of such compositions has been found ineffective for treatment of diseases at the back of the eye such as AMD, diabetic retinopathy and many others. The ophthalmic pharmaceutical industry has generally been unable to find drugs that, upon topical dosing, penetrate the cornea, sclera and/or conjunctiva in a manner that provides sufficient drug concentration to the back of the eye. Thus, finding a drug that will penetrate the cornea, sclera and/or conjunctiva is a significant achievement in itself. Even upon finding such a drug, however, other obstacles have prevented those drugs from being effectively formulated into topical aqueous ophthalmic compositions that can be applied to the eye safely, effectively and efficaciously. For example, it may be necessary to provide a very high concentration of drug in the composition to achieve efficacy, but such a concentration can cause side effects such as toxicity and undesirable systemic exposure. As another example, such a drug may be difficult to provide in an aqueous composition due to hydrophobicity of the drug, high reactivity of the drug with excipients commonly used in topical ophthalmic compositions or for other reasons.

Agglomeration can be particularly troublesome for the hydrophobic ophthalmic drugs discussed herein. It is known that hydrophobic drugs are particularly prone to agglomeration within aqueous topical ophthalmic compositions and such agglomeration can be particularly difficult to counteract and can cause stability and potentially other quality issues for the compositions. Moreover, it has been found that additional or alternative causes for agglomeration of drugs can be exist in an ophthalmic composition and can be particularly difficult to identify due to the expectation that agglomeration is due to hydrophobicity of the drugs. In such circumstances, the additional or alternative causes can be quite varied and unexpected making those causes particularly difficult to address.

In view of the above, it would be particularly desirable to provide an ophthalmic composition, which can be dosed topically, can provide a drug to the back of the eye at a desired concentration to treat a disease at or associated with the back of the eye and avoids problems encountered when the ophthalmic pharmaceutical industry has previously attempted to topically dose a drug to treat the back of the eye.

SUMMARY OF THE INVENTION

According to the present invention, there is provided a multi-dose aqueous ophthalmic composition. The composition includes an effective concentration of a 1H-indole-1-carboxamide suitable to treat a condition at the back of the eye, wherein the 1H-indole-1-carboxamide is a compound from formula I below:

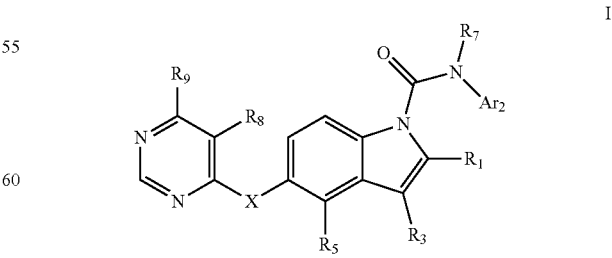

or a pharmaceutically acceptable salt thereof, wherein:
$R_1$ is hydrogen or $C_1$-$C_6$alkyl;
$R_3$ is hydrogen or $C_1$-$C_6$alkyl;
$R_5$ is hydrogen or halogen;

$R_7$ is hydrogen or $C_1$-$C_6$alkyl;

X is O or S;

$R_8$ is selected from the group consisting of hydrogen and $C_1$-$C_4$alkyl;

$R_9$ is selected from the group consisting of $(CR_{11}R_{12})_n$ $NR_{13}R_{14}$, $(CR_{11}R_{12})_n$heterocycle, $(CR_{11}R_{12})_n OR_{14}$, $(CR_{11}R_{12})_n C(O)ER_{13}$, and $(CR_{11}R_{12})_n S(O)_m R_{17}$; or $R_8$ and $R_9$, taken in combination together with the atoms to which they are attached form a saturated 4-7 membered heterocyclic ring having 1 or 2 ring heteroatoms selected from N, O or S, which heterocyclic ring is substituted with 0, 1, or 2 groups independently selected from the group consisting of $C_1$-$C_6$alkyl, $C_1$-$C_6$haloalkyl, halogen, hydroxy$C_1$-$C_6$alkyl, amino$C_1$-$C_6$alkyl, $C_3$-$C_7$cycloalkyl$C_1$-$C_4$alkyl, heterocycle$C_1$-$C_4$alkyl, $C_1$-$C_6$alkanoyl, mono- and di-$C_1$-$C_6$alkylaminocarbonyl, $C_1$-$C_6$alkoxycarbonyl, and $C_1$-$C_6$alkylsulfonyl;

$Ar_2$ is phenyl, naphthyl, 5 or 6 membered monocyclic heteroaryl, wherein each heteroaryl has 1, 2, or 3 ring heteroatoms selected from N, O or S and wherein the phenyl, naphthyl, or heteroaryl group is unsubstituted or substituted by 1, 2, or 3 groups independently selected from the group consisting of $C_1$-$C_6$alkyl, $C_1$-$C_6$haloalkyl, halo, hydroxyl, $CO_2C_1$-$C_6$alkyl, phenyl, and $C_3$-$C_7$cycloalkyl;

m is 0, 1, or 2;

n is 1, 2, or 3;

E is O or $NR_{18}$;

$R_{11}$, $R_{12}$ and $R_{18}$ are the same or different and are independently selected at each occurrence from the group consisting of hydrogen and $C_1$-$C_4$alkyl; and $R_{13}$, $R_{14}$, $R_{15}$, $R_{16}$ and $R_{17}$ are independently selected at each occurrence from the group consisting of hydrogen, $C_1$-$C_6$alkyl, $C_3$-$C_6$cycloalkyl, phenyl and heterocycle, each of which is substituted with 0, 1 or 2 groups independently selected from hydroxyl, amino, and mono- and di-$C_1$-$C_6$alkylamino. The composition further includes an ophthalmic vehicle comprised at least 80 w/v % water and two or more ingredients selected from the group consisting of a surfactant, a buffer, a polyol, a suspending agent, an osmolality agent and a preservative. The composition preferably has a pH in the range of 4 to 9 and an osmolality of 200 to 450 mOsm/kg.

In a preferred embodiment, the ophthalmic composition includes the buffer and the polyol and wherein the buffer is borate. In an additional or alternative preferred embodiment, the polyol includes mannitol and/or sorbitol and/or the polyol includes propylene glycol and/or glycerol. The mannitol and/or sorbitol, when present in the composition, is/are preferably in the composition at a concentration that is greater than about 0.15 w/v % but less than about 0.5 w/v %. The propylene glycol and/or glycerol, when present in the composition, is/are preferably in the composition at a concentration that is greater than about 0.5 w/v % but less than about 1.8 w/v %. The borate, when present in the composition, is preferably in the composition at a concentration that is greater than about 0.1 w/v % but less than about 0.4 w/v %.

In an additional or alternative preferred embodiment, the preservative is present in the composition and is selected from the group consisting of benzalkonium chloride and polymeric quaternary ammonium compound. In a further additional or alternative preferred embodiment, the pH of the composition is in the range 6.0 to 7.8 and the osmolality of the composition is in the range 240 to 360 mOsm/kg.

In an additional or alternative preferred embodiment, the 1H-indole-1-carboxamide is 1H-indole-1-carboxamide is N-(1-methyl-5-(trifluoromethyl)-1H-pyrazol-3-yl)-5-((6-((methylamino)methyl)pyrimidin-4-yl)oxy)-1H-indole-1-carboxamide. Preferably, the concentration of 1H-indole-1-carboxamide, particularly N-(1-methyl-5-(trifluoromethyl)-1H-pyrazol-3-yl)-5-((6-((methylamino)methyl)pyrimidin-4-yl)oxy)-1H-indole-1-carboxamide, in the composition is greater than about 0.1 w/v %, more typically greater than about 0.4 w/v %, even more typically greater than about 1.0 w/v % and potentially greater than about 1.8 w/v % and even possibly greater than 2.5 w/v % but typically less than about 5.0 w/v %, more typically less than about 4.0 w/v % and even more typically less than about 3.3 w/v % and even possibly less than about 2.3 w/v %.

Additionally or alternatively, the 1H-indole-1-carboxamide, particularly N-(1-methyl-5-(trifluoromethyl)-1H-pyrazol-3-yl)-5-((6-((methylamino)methyl)pyrimidin-4-yl)oxy)-1H-indole-1-carboxamide, is in the composition at a concentration that is in one of the following ranges: greater than about 0.4 w/v % but less than about 4.0 w/v %; greater than about 0.4 w/v % but less than about 3.3 w/v %; greater than about 1.8 w/v % but less than about 4.0 w/v %; and greater than about 1.8 w/v % but less than about 3.3 w/v %.

In another additional or alternative embodiment, the ophthalmic composition includes the suspending agent. Preferably, the suspending agent is a cellulosic derivative. More preferably, the suspending agent is hydroxyethyl cellulose (HEC). When present in the composition, the cellulosic derivative, particularly HEC, is in the composition at a concentration that is greater than about 0.25 w/v % but less than about 0.7 w/v %. For HEC, the preferred weight average molecular weight is typically from about 50,000 to about 2,000,000, more typically from about 250,000 to about 1,500,000, even more typically from about 700,000 to about 1,300,000 and still more typically from about 900,000 to about 1,100,000.

In another additional or alternative embodiment, the 1H-indole-1-carboxamide is an anti-angiogenic agent and/or anti-neovascularization agent and treats (i.e., inhibits, halts and/or potentially reverses) the condition at the back of the eye wherein the condition at the back of the eye is angiogenesis and/or neovascularization at the retina or the posterior eye cup of the eye. As another additional or alternative embodiment, the 1H-indole-1-carboxamide treats conditions mediated by a protein kinase, specifically protein tyrosine kinase, more specifically VEGF receptor at the back of the eye wherein the condition at the back of the eye is angiogenesis and/or neovascularization at the retina or the posterior eye cup of the eye. The condition at the back of the eye of the eye is preferably selected from the group consisting of age related macular degeneration (AMD) (wet or dry), central serous retinopathy, cystoid macular edema, diabetic retinopathy, proliferative diabetic retinopathy, diabetic macular edema, rubeosis iridis, retinopathy of prematurity, central and branch retinal vein occlusions, inflammatory/infectious retinal neovascularization/edema (e.g. posterior uveitis, sarcoid, toxoplasmosis, histoplasmosis, Vogt-Koyanagi-Harada Disease, chronic uveitis, tuberculsosis, syphyllis, punctate and multifocal inner choroidopathy), retinoblastoma, ocular melanoma, ocular tumors, retinal detachment, myopic neovascularization, angiod streaks, Eales disease, ischemic retinopathy (retinal artery occlusion, Takayasu's, carotid artery occlusion), choroidal rupture or any combination thereof. In one highly preferred embodiment, the condition at the back of the eye is age related macular degeneration (AMD).

In a highly preferred embodiment, the ophthalmic composition when in suspension form such as described using HEC as a suspending agent, the composition will additionally include a charged and/or salt form CMC to ameliorate agglomeration of the 1H-indole-1-carboxamide. Preferably, the charged and/or salt form CMC is NaCMC. The concentration of suspending agent, particularly HEC, in the composition is at least about 0.05 w/v %, more typically at least about 0.1 w/v % and still more typically at least about 0.15 w/v %. and less than about 0.7 w/v %, more typically less than about 0.5 w/v % and still more typically less than about 0.3 w/v %. Additionally or alternatively, the concentration of the suspending agent, particularly HEC, is at least about 0.05 w/v % but less than about 0.7 w/v %; at least about 0.1 w/v % but less than about 0.5 w/v %; at least about 0.15 w/v % but less than about 0.3 w/v %. The concentration of charged and/or salt form CMC, particularly NaCMC, in the composition is at least about 0.3 w/v %, more typically at least about 0.6 w/v % and still more typically at least about 0.8 w/v % but is typically no greater than about 2.0 w/v %, more typically no greater than about 1.5 w/v % and still more typically no greater than about 1.3 w/v %. Additionally or alternatively, the concentration of charged and/or salt form CMC, NaCMC, is at least about 0.3 w/v % but no greater than about 2.0 w/v %; at least about 0.6 w/v % but no greater than about 1.5 w/v %; at least about 0.8 w/v % but no greater than about 1.3 w/v %. In such embodiment, the viscosity of the composition is at least 5 centipoise (cP), more at least about 12 cP and still more typically at least about 20 cP and is typically less than about 100 cP, more typically less than about 65 cP and still more typically less than about 50 cP. Additionally or alternatively, the viscosity of the composition is at least about 5 cP but no greater than about 100 cP at least about 15 cP but no greater than about 65 cP; at least about 20 cP but no greater than about 50 cP.

In another particularly preferred alternative or additional embodiment, the 1H-indole-1-carboxamide is dissolved in solution to form a topical aqueous composition as opposed to having the 1H-indole-1-carboxamide suspended. In such embodiment, the composition preferably further comprises a cyclodextrin derivative selected from the group consisting of β-cyclodextrin derivative, γ-cyclodextrin derivative and a combination thereof. More preferably, the cyclodextrin derivative is selected from the group consisting of hydroxypropy-β-cyclodextrin, hydroxypropyl-γ-cyclodextrin and a combination thereof. When present, the cyclodextrin derivative is typically in the composition at a concentration that is at least 1.5 w/v %, more typically at least 3.0 w/v %, even more possibly at least 3.5 w/v % and even possibly at least 4.5 w/v, but is typically no greater than about 10.0 w/v %, more typically no greater than about 7.2% w/v, even more typically no greater than about 5.5 w/v % and even possibly no greater than 4.5 w/v and/or wherein the cyclodextrin derivative is present in the composition at concentration that is at least 1.5 w/v % but no greater than 10.0 w/v %, more typically at least 3.5 w/v % but no greater than 7.2 w/v % and even more typically at least 4.5 w/v % but no greater than 5.5 w/v %. To aid in dissolution of the 1H-indole-1-carboxamide, the composition (i.e., solution) preferably has a pH that is at least 4.0 and even more typically at least 4.3, but is typically no greater than 5.5, more typically no greater than 5.0 and even more typically no greater than 4.7 and/or the composition has a pH that is at least 4.0 but no greater than 5.0 and more preferably at least 4.3 but no greater than 4.7. To yet further aid in solubilizing the 1H-indole-1-carboxamide, the composition further comprises a pH adjustment agent selected from the group consisting of sulfuric acid, phosphoric acid, lactic acid, acetic acid, glucoronic acid or methasulfonic acid and combinations thereof. Even more preferably, the pH adjustment agent is selected from the group consisting of sulfuric acid, phosphoric acid, acetic acid, lactic acid and combinations thereof. Sulfuric acid is particularly preferred as a substantial portion (at least 70 wt. %), substantially the entirety (at least 90 wt %) or the entirety of the pH adjustment. The pH adjustment agent is in the composition at a concentration that is at least 0.001 w/v %, more typically at least 0.05 w/v % and even more typically at least 0.5 w/v % but less than 5.0 w/v %. Thus, the pH adjustment agent is preferably in the composition at a concentration that is at is at least 0.001 w/v % but less than 5.0 w/v %, more typically at least 0.05 w/v % but less than 5.0 w/v % and even more typically at least 0.5 w/v % but less than 5.0 w/v %.

In another additional or alternative embodiment, the composition is disposed within a dispenser configured to deliver the composition to a cornea of an eye. The dispenser is preferably an eyedropper that dispenses individual drops of the composition to the outer surface of the cornea of the eye.

The present invention is also directed to a method of treating the eye. The method comprising topically dispensing the composition in any of it above or below discussed embodiments to a cornea of the eye and, when disposed in a dispenser, the ophthalmic composition is dispensed the cornea of the eye using the dispenser.

DETAILED DESCRIPTION OF THE INVENTION

Figure 1:
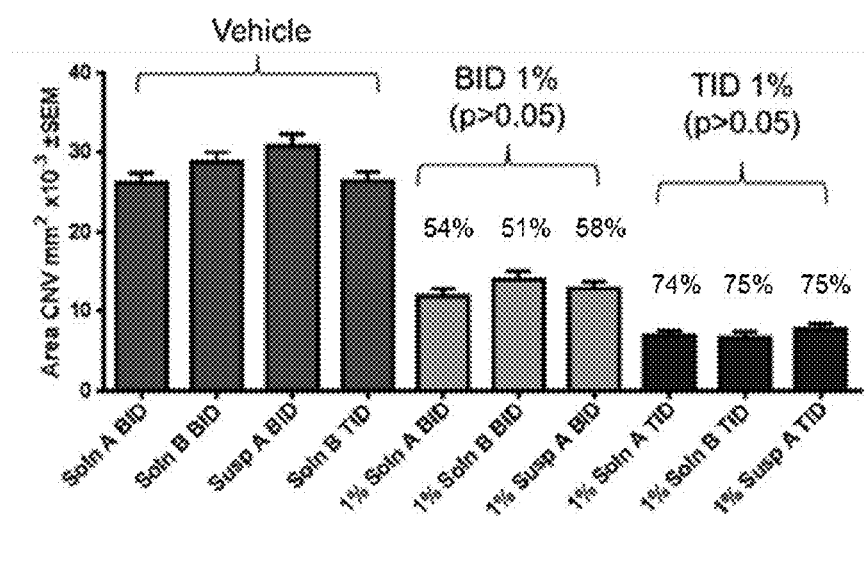
FIG. 1 is a graph illustrating the potency and efficacy of multiple different multi-dose topical ophthalmic compositions containing a 1H-indole-1-carboxamide as compared to a control.

The present invention is predicated upon the provision of a multi-dose topical ophthalmic composition containing a 1H-indole-1-carboxamide wherein the composition can be dosed as drops or otherwise topically to the eye and effectively treat an ophthalmic disease at the back of the eye. The ophthalmic condition (e.g., disease) to be treated can be any disease that causes or is typified by the presence of angiogenesis and/or neovascularization. Thus, the 1H-indole-1-carboxamide of the present invention is an anti-angiogenic agent and/or anti-neovascularization agent and treats (i.e., inhibits, halts and/or potentially reverses) angiogenesis and/or neovascularization at the retina or the posterior eye cup. As used herein, the posterior eye cup includes the choroid, the retinal pigment epithelium, and the sclera. However, treatment of the posterior eye cup can include treatment of any one or any combination of the choroid, the retinal pigment epithelium, and the sclera. Additionally or alternatively the 1H-indole-1-carboxamide treats conditions mediated by a protein kinase, specifically protein tyrosine kinase, more specifically VEGF receptor at the back of the eye wherein the condition at the back of the eye is angiogenesis and/or neovascularization at the retina or the posterior eye cup of the eye.

Examples of ophthalmic conditions and diseases, which affect the back of the eye and which can be treated with the composition of the present invention containing the 1H-indole-1-carboxamide include, without limitation, age related macular degeneration (AMD) (wet or dry), central serous retinopathy, cystoid macular edema, diabetic retinopathy, proliferative diabetic retinopathy, diabetic macular edema, rubeosis iridis, retinopathy of prematurity, central and branch retinal vein occlusions, inflammatory/infectious retinal neovascularization/edema (e.g. posterior uveitis, sarcoid, toxoplasmosis, histoplasmosis, Vogt-Koyanagi-Harada Disease, chronic posterior uveitis, tuberculosis, syphilis, punctate and multifocal inner choroidopathy), retinoblastoma, ocular melanoma, ocular tumors, retinal detachment, myopic neovascularization, angiod streaks, Eales disease, ischemic retinopathy (retinal artery occlusion, Takayasu's, carotid artery occlusion), choroidal rupture or any combination thereof.

It shall be understood that treatment of diseases or conditions that affect the back of the eye are a particularly advantageous and surprising aspect of the ophthalmic composition of the present invention since the ophthalmic composition is for topical application. The skilled artisan will, however, upon reading the disclosure herein, understand that the ophthalmic composition could be employed to treat conditions or diseases at the front of the eye such as contact lens wear conditions, dry eye, blepharitis, corneal dystrophies, trauma and previous surgery to the cornea (corneal grafts, LASIK, LASEK), corneal infections (bacterial, viral, parasitic, herpetic), corneal burns (chemical, alkali, acid), corneal graft rejection, immunological corneal disease (pemhigoid, Stevens-Johnsons syndrome), and degenerative corneal diseases or any combination thereof.

In a preferred embodiment, the ophthalmic composition of the present invention can be dosed topically to the eye and effectively treat one or more of these conditions of the retina or posterior eye cup. The composition is preferably an aqueous composition (i.e., a solution, a suspension or an emulsion). In a highly preferred embodiment, the aqueous composition is a suspension that employs a cellulosic material as a suspending agent.

Unless otherwise indicated, percentages provided for the ingredients of the ophthalmic composition of the present invention are weight/volume (w/v) percentages.

As used herein, the term "borate" shall refer to boric acid, salts of boric acid, borate derivatives and other pharmaceutically acceptable borates, or combinations thereof. Most suitable are: boric acid, sodium borate, potassium borate, calcium borate, magnesium borate, manganese borate, and other such borate salts.

As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol, sorbitol and propylene glycol, combinations thereof or the like. Borate can interact with polyol to form borate polyol complexes. The type and ratio of such complexes depends on the number of OH groups of a polyol on adjacent carbon atoms that are not in trans configuration relative to each other. It shall be understood that weight/volume percentages of the ingredients polyol and borate include those amounts whether as part of a complex or not.

As utilized herein, the phrase "less than" relative to a specified concentration (e.g., 1 w/v %) means that the specified component (e.g., antimicrobial preservative) is either not present in the composition at all or is present at a concentration less than the specified limit (e.g., 1 w/v %)).

As utilized herein, the phrase "an effective amount of" means that a specified component is present in the composition in an amount sufficient to have an impact on the therapeutic capability, the buffering capability, the preservative capability and/or the anti-microbial capability of the composition.

As used herein, the phrase "substantially free of" as it refers to an ingredient of the ophthalmic composition means that it is contemplated that the ophthalmic solution can be either entirely devoid of that particular ingredient or includes only a nominal amount of that particular ingredient.

The synthesis and associated physical and biological data for specific 1H-compounds disclosed in international patent publication WO2010/066685 is incorporated herein by reference. Said compounds and compositions are suitable for use in the present invention.

As used herein, a 1H-indole-1-carboxamide refers to a compound of the formula I below:

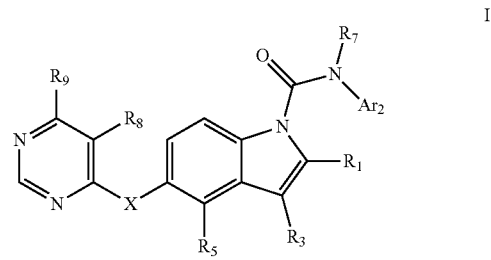

or a pharmaceutically acceptable salt thereof, wherein:
$R_1$ is hydrogen or $C_1$-$C_6$alkyl;
$R_3$ is hydrogen or $C_1$-$C_6$alkyl;
$R_5$ is hydrogen or halogen;
$R_7$ is hydrogen or $C_1$-$C_6$alkyl;
X is O or S;
$R_8$ is selected from the group consisting of hydrogen and $C_1$-$C_4$alkyl;
$R_9$ is selected from the group consisting of $(CR_{11}R_{12})_n NR_{13}R_{14}$, $(CR_{11}R_{12})_n$heterocycle, $(CR_{11}R_{12})_n OR_{15}$, $(CR_{11}R_{12})_n C(O)ER_{13}$, and $(CR_{11}R_{12})_n S(O)_m R_{17}$; or
$R_8$ and $R_9$, taken in combination together with the atoms to which they are attached form a saturated 4-7 membered heterocyclic ring having 1 or 2 ring heteroatoms selected from N, O or S, which heterocyclic ring is substituted with 0, 1, or 2 groups independently selected from the group consisting of $C_1$-$C_6$alkyl, $C_1$-$C_6$haloalkyl, halogen, hydroxy$C_1$-$C_6$alkyl, amino$C_1$-$C_6$alkyl, $C_3$-$C_7$cycloalkyl$C_1$-$C_4$alkyl, heterocycle$C_1$-$C_4$alkyl, $C_1$-$C_6$alkanoyl, mono- and di-$C_1$-$C_6$alkylaminocarbonyl, $C_1$-$C_6$alkoxycarbonyl, and $C_1$-$C_6$alkylsulfonyl;
$Ar_2$ is phenyl, naphthyl, 5 or 6 membered monocyclic heteroaryl, wherein each heteroaryl has 1, 2, or 3 ring heteroatoms selected from N, O or S and wherein the phenyl, naphthyl, or heteroaryl group is unsubstituted or substituted by 1, 2, or 3 groups independently selected from the group consisting of $C_1$-$C_6$alkyl, $C_1$-$C_6$haloalkyl, halo, hydroxyl, $CO_2C_1$-$C_6$alkyl, phenyl, and $C_3$-$C_7$cycloalkyl;

m is 0, 1, or 2;

n is 1, 2, or 3;

E is O or $NR_{18}$;

$R_{11}$, $R_{12}$ and $R_{18}$ are the same or different and are independently selected at each occurrence from the group consisting of hydrogen and $C_1$-$C_4$alkyl; and $R_{13}$, $R_{14}$, $R_{15}$, $R_{16}$ and $R_{17}$ are independently selected at each occurrence from the group consisting of hydrogen, $C_1$-$C_6$alkyl, $C_3$-$C_6$cycloalkyl, phenyl and heterocycle, each of which is substituted with 0, 1 or 2 groups independently selected from hydroxyl, amino, and mono- and di-$C_1$-$C_6$alkylamino.

Examples of preferred 1H-indole-1-carboxamides include, without limitation, the following:

N-(4-fluoro-3-(trifluoromethyl)phenyl)-5-(6-((methylamino)methyl)pyrimidin-4-yloxy)-1H-indole-1-carboxamide;

5-(6-(hydroxymethyl)pyrimidin-4-yloxy)-N-(3-(trifluoromethyl)phenyl)-1H-indole-1-carboxamide;

5-(6-(methoxymethyl)pyrimidin-4-yloxy)-N-(3-(trifluoromethyl)phenyl)-1H-indole-1-carboxamide;

5-(6-((methylamino)methyl)pyrimidin-4-yloxy)-N-(3-(trifluoromethyl)phenyl)-1H-indole-1-carboxamide;

5-(6-((dimethylamino)methyl)pyrimidin-4-yloxy)-N-(3-(trifluoromethyl)phenyl)-1H-indole-1-carboxamide;

5-(2-((methylamino)methyl)pyridin-4-yloxy)-N-(3-(trifluoromethyl)phenyl)-1H-indole-1-carboxamide;

5-(6-((2H-tetrazol-2-yl)methyl)pyrimidin-4-yloxy)-N-(4-fluoro-3-(trifluoromethyl)phenyl)-1H-indole-1-carboxamide;

5-(6-((cyclopropylamino)methyl)pyrimidin-4-yloxy)-N-(4-fluoro-3-(trifluoromethyl)phenyl)-1H-indole-1-carboxamide;

N-(2-fluoro-3-(trifluoromethyl)phenyl)-5-(6-((methylamino)methyl)pyrimidin-4-yloxy)-1H-indole-1-carboxamide;

5-(6-((cyclopropylamino)methyl)pyrimidin-4-yloxy)-N-(2-fluoro-3-(trifluoromethyl)phenyl)-1H-indole-1-carboxamide;

N-(4-fluoro-3-(trifluoromethyl)phenyl)-5-(6-(methylsulfonylmethyl)pyrimidin-4-yloxy)-1H-indole-1-carboxamide;

5-(7-ethyl-5,6,7,8-tetrahydropyrido[3,4-d]pyrimidin-4-yloxy)-N-(4-fluoro-3-(trifluoromethyl)phenyl)-1H-indole-1-carboxamide;

5-(7-propyl-5,6,7,8-tetrahydropyrido[3,4-d]pyrimidin-4-yloxy)-N-(3-(trifluoromethyl)phenyl)-1H-indole-1-carboxamide;

5-(7-isopropyl-5,6,7,8-tetrahydropyrido[3,4-d]pyrimidin-4-yloxy)-N-(3-(trifluoromethyl)phenyl)-1H-indole-1-carboxamide;

5-(7-methyl-5,6,7,8-tetrahydropyrido[3,4-d]pyrimidin-4-yloxy)-N-(3-(trifluoromethyl)phenyl)-1H-indole-1-carboxamide;

5-(6,7-dihydro-5H-pyrrolo[3,4-d]pyrimidin-4-yloxy)-N-(3-(trifluoromethyl)phenyl)-1H-indole-1-carboxamide;

4-fluoro-5-(5,6,7,8-tetrahydropyrido[3,4-d]pyrimidin-4-yloxy)-N-(3-(trifluoromethyl)phenyl)-1H-indole-1-carboxamide;

5-(6-((methylamino)methyl)pyrimidin-4-yloxy)-N-(3-(trifluoromethyl)-1H-pyrazol-5-yl)-1H-indole-1-carboxamide;

N-(2-fluoro-5-(trifluoromethyl)phenyl)-5-(5,6,7,8-tetrahydropyrido[3,4-d]pyrimidin-4-yloxy)-1H-indole-1-carboxamide;

4-fluoro-5-(6-((methylamino)methyl)pyrimidin-4-yloxy)-N-(5-(trifluoromethyl)-1H-pyrazol-3-yl)-1H-indole-1-carboxamide;

N-(5-tert-butylisoxazol-3-yl)-4-fluoro-5-(5,6,7,8-tetrahydropyrido[3,4-d]pyrimidin-4-yloxy)-1H-indole-1-carboxamide;

5-(6,7-dihydro-5H-pyrrolo[3,4-d]pyrimidin-4-yloxy)-4-fluoro-N-(2-fluoro-3-(trifluoromethyl)phenyl)-1H-indole-1-carboxamide;

N-(5-tert-butylisoxazol-3-yl)-5-(6-methyl-6,7-dihydro-5H-pyrrolo[3,4-d]pyrimidin-4-yloxy)-1H-indole-1-carboxamide;

4-fluoro-5-(6-(hydroxymethyl)pyrimidin-4-yloxy)-N-(3-(trifluoromethyl)phenyl)-1H-indole-1-carboxamide;

N-(2-fluoro-3-(trifluoromethyl)phenyl)-5-(6-(methylsulfonylmethyl)pyrimidin-4-yloxy)-1H-indole-1-carboxamide;

N-(5-cyclopropylisoxazol-3-yl)-5-(6,7-dihydro-5H-pyrrolo[3,4-d]pyrimidin-4-yloxy)-1H-indole-1-carboxamide;

N-(3-isopropyl-1H-pyrazol-5-yl)-5-(6-methyl-5,6,7,8-tetrahydropyrido[3,4-d]pyrimidin-4-yloxy)-1H-indole-1-carboxamide;

N-(3-cyclopropyl-1H-pyrazol-5-yl)-5-(6-methyl-5,6,7,8-tetrahydropyrido[3,4-d]pyrimidin-4-yloxy)-1H-indole-1-carboxamide;

(S)—N-(5-cyclopropylisoxazol-3-yl)-5-(6-methyl-5,6,7,8-tetrahydropyrido[3,4-d]pyrimidin-4-yloxy)-1H-indole-1-carboxamide;

5-(6,7-dihydro-5H-pyrrolo[3,4-d]pyrimidin-4-yloxy)-N-(5-(1-(trifluoromethyl)cyclopropyl)isoxazol-3-yl)-1H-indole-1-carboxamide;

N-(5-cyclopropyl-4-methylisoxazol-3-yl)-5-(6,7-dihydro-5H-pyrrolo[3,4-d]pyrimidin-4-yloxy)-1H-indole-1-carboxamide;

5-(5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

5-(6-methyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

5-(6-((2H-tetrazol-2-yl)methyl)pyrimidin-4-yloxy)-N-(5-cyclopropylisoxazol-3-yl)-1H-indole-1-carboxamide;

N-(5-isopropylisoxazol-3-yl)-5-(6-((methylamino)methyl)pyrimidin-4-yloxy)-1H-indole-1-carboxamide;

(S)—N-(3-isopropyl-1H-pyrazol-5-yl)-5-(6-methyl-5,6,7,8-tetrahydropyrido[3,4-d]pyrimidin-4-yloxy)-1H-indole-1-carboxamide;

N-(1-methyl-5-(1-methylcyclopropyl)-1H-pyrazol-3-yl)-5-(5,6,7,8-tetrahydropyrido[3,4-d]pyrimidin-4-yloxy)-1H-indole-1-carboxamide;

5-(6-((2H-tetrazol-2-yl)methyl)pyrimidin-4-yloxy)-N-(5-isopropylisoxazol-3-yl)-1H-indole-1-carboxamide;

5-(6-((methylamino)methyl)pyrimidin-4-yloxy)-N-(5-(1-methylcyclopropyl)isoxazol-3-yl)-1H-indole-1-carboxamide;

(S)—N-(5-cyclopropylisoxazol-3-yl)-5-(7-ethanoyl-6-methyl-5,6,7,8-tetrahydropyrido[3,4-d]pyrimidin-4-yloxy)-1H-indole-1-carboxamide;

(S)—N-(5-cyclopropylisoxazol-3-yl)-5-(7-ethyl-6-methyl-5,6,7,8-tetrahydropyrido[3,4-d]pyrimidin-4-yloxy)-1H-indole-1-carboxamide;

N-(5-cyclopropylisoxazol-3-yl)-5-(7-ethanoyl-5,6,7,8-tetrahydropyrido[3,4-d]pyrimidin-4-yloxy)-1H-indole-1-carboxamide 5-(6-((2H-tetrazol-2-yl)methyl)pyrimidin-4-yloxy)-N-(5-(1-methylcyclopropyl)isoxazol-3-yl)-1H-indole-1-carboxamide;

(S)-5-(7-ethyl-6-methyl-5,6,7,8-tetrahydropyrido[3,4-d]pyrimidin-4-yloxy)-N-(3-(1-methylcyclopropyl)-1H-pyrazol-5-yl)-1H-indole-1-carboxamide;

(S)-5-(6-methyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide (S)—N-(5-cyclopropylisoxazol-3-yl)-5-(6-methyl-7-(methylsulfonyl)-5,6,7,8-tetrahydropyrido[3,4-d]pyrimidin-4-yloxy)-1H-indole-1-carboxamide;

5-(5,7-dihydrothieno[3,4-d]pyrimidin-4-yloxy)-N-(3-(trifluoromethyl)phenyl)-1H-indole-1-carboxamide;

5-(5,7-dihydrothieno[3,4-d]pyrimidin-4-yloxy)-N-(5-(1-methylcyclopropyl)isoxazol-3-yl)-1H-indole-1-carboxamide;

(S)-5-(7-ethanoyl-6-methyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

(S)-5-(7-ethyl-6-methyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

4-chloro-5-(6,7-dihydro-5H-pyrrolo[3,4-d]pyrimidin-4-yloxy)-N-(5-isopropylisoxazol-3-yl)-1H-indole-1-carboxamide;

(S)—N-(4,4-dimethyl-5,6-dihydro-4H-pyrrolo[1,2-b]pyrazol-2-yl)-5-(6-methyl-5,6,7,8-tetrahydropyrido[3,4-d]pyrimidin-4-yloxy)-1H-indole-1-carboxamide;

5-(6,7-dihydro-5H-pyrrolo[3,4-d]pyrimidin-4-yloxy)-N-(4-methyl-5-(1-methylcyclopropyl)isoxazol-3-yl)-1H-indole-1-carboxamide;

N-(5-tert-butyl-4-methylisoxazol-3-yl)-5-(6,7-dihydro-5H-pyrrolo[3,4-d]pyrimidin-4-yloxy)-1H-indole-1-carboxamide;

5-(6,7-dihydro-5H-pyrrolo[3,4-d]pyrimidin-4-yloxy)-N-(5-isopropyl-4-methylisoxazol-3-yl)-1H-indole-1-carboxamide;

N-(5-cyclopropylisoxazol-3-yl)-5-(6,7,8,9-tetrahydro-5H-pyrimido[4,5-c]azepin-4-yloxy)-1H-indole-1-carboxamide;

(S)-5-(6-methyl-5,6,7,8-tetrahydropyrido[3,4-d]pyrimidin-4-yloxy)-N-(1-methyl-5-(1-methylcyclopropyl)-1H-pyrazol-3-yl)-1H-indole-1-carboxamide;

(S)-5-(6-methyl-5,6,7,8-tetrahydropyrido[3,4-d]pyrimidin-4-yloxy)-N-(5-(4,4,4-trifluoro-2-methylbutan-2-yl)isoxazol-3-yl)-1H-indole-1-carboxamide;

5-(6,7,8,9-tetrahydro-5H-pyrimido[4,5-c]azepin-4-yloxy)-N-(5-(1-(trifluoromethyl)cyclopropyl)isoxazol-3-yl)-1H-indole-1-carboxamide;

N-(4-chloro-5-(1-methylcyclopropyl)isoxazol-3-yl)-5-(6,7-dihydro-5H-pyrrolo[3,4-d]pyrimidin-4-yloxy)-1H-indole-1-carboxamide;

(S)-5-(7-(cyclopropylmethyl)-6-methyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

N-(5-tert-butylisoxazol-3-yl)-5-(6,7,8,9-tetrahydro-5H-pyrimido[4,5-c]azepin-4-yloxy)-1H-indole-1-carboxamide;

5-(6-ethanoyl-6,7-dihydro-5H-pyrrolo[3,4-d]pyrimidin-4-yloxy)-N-(2-fluoro-3-(trifluoromethyl)phenyl)-1H-indole-1-carboxamide;

5-(6-ethanoyl-6,7-dihydro-5H-pyrrolo[3,4-d]pyrimidin-4-yloxy)-N-(5-(1-methylcyclopropyl)isoxazol-3-yl)-1H-indole-1-carboxamide;

5-(6-ethanoyl-6,7-dihydro-5H-pyrrolo[3,4-d]pyrimidin-4-yloxy)-N-(5-isopropylisoxazol-3-yl)-1H-indole-1-carboxamide;

N-(5-cyclopropylisoxazol-3-yl)-5-(6-ethanoyl-6,7-dihydro-5H-pyrrolo[3,4-d]pyrimidin-4-yloxy)-1H-indole-1-carboxamide;

5-(6,7-dihydro-5H-pyrrolo[3,4-d]pyrimidin-4-yloxy)-N-(1-isopropyl-5-methyl-1H-pyrazol-3-yl)-1H-indole-1-carboxamide;

(S)-5-(7-(cyclopropanecarbonyl)-6-methyl-5,6,7,8-tetrahydropyrido[3,4-d]pyrimidin-4-yloxy)-N-(5-cyclopropylisoxazol-3-yl)-1H-indole-1-carboxamide;

(S)—N-(5-cyclopropylisoxazol-3-yl)-5-(6,7-dimethyl-5,6,7,8-tetrahydropyrido[3,4-d]pyrimidin-4-yloxy)-1H-indole-1-carboxamide;

(S)-5-(6-methyl-7-(2-methylpropanoyl)-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide (S)-5-(6-methyl-7-(3-methylbutanoyl)-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

5-(5,7-dihydrothieno[3,4-d]pyrimidin-4-yloxy)-N-(5-(1-(trifluoromethyl)cyclopropyl)isoxazol-3-yl)-1H-indole-1-carboxamide;

5-(5,7-dihydrothieno[3,4-d]pyrimidin-4-yloxy)-N-(2-fluoro-3-(trifluoromethyl)phenyl)-1H-indole-1-carboxamide;

N-(4,4-dimethyl-5,6-dihydro-4H-pyrrolo[1,2-b]pyrazol-2-yl)-5-(6-(methylsulfonylmethyl)pyrimidin-4-yloxy)-1H-indole-1-carboxamide;

5-(6-(cyclopropanecarbonyl)-6,7-dihydro-5H-pyrrolo[3,4-d]pyrimidin-4-yloxy)-N-(5-(1-(trifluoromethyl)cyclopropyl)isoxazol-3-yl)-1H-indole-1-carboxamide;

5-(6-(2-methylpropanoyl)-6,7-dihydro-5H-pyrrolo[3,4-d]pyrimidin-4-yloxy)-N-(5-(1-(trifluoromethyl)cyclopropyl)isoxazol-3-yl)-1H-indole-1-carboxamide;

N-(4,4-dimethyl-5,6-dihydro-4H-pyrrolo[1,2-b]pyrazol-2-yl)-5-(6,7,8,9-tetrahydro-5H-pyrimido[4,5-c]azepin-4-yloxy)-1H-indole-1-carboxamide;

5-(6-((methylamino)methyl)pyrimidin-4-yloxy)-N-(5-(1-methylcyclopropyl)-1H-pyrazol-3-yl)-1H-indole-1-carboxamide;

5-(6,7-dihydro-5H-pyrrolo[3,4-d]pyrimidin-4-yloxy)-N-(5-isopropylisoxazol-3-yl)-4-methyl-1H-indole-1-carboxamide;

N-(5-isopropyl-1H-pyrazol-3-yl)-5-(6-((methylamino)methyl)pyrimidin-4-yloxy)-1H-indole-1-carboxamide;

(S)—N-(5-cyclopropylisoxazol-3-yl)-5-(7-(2-hydroxyethyl)-6-methyl-5,6,7,8-tetrahydropyrido[3,4-d]pyrimidin-4-yloxy)-1H-indole-1-carboxamide;

N-(5-cyclopropylisoxazol-3-yl)-5-(6,7-dihydro-5H-pyrrolo[3,4-d]pyrimidin-4-yloxy)-4-methyl-1H-indole-1-carboxamide;

5-(6-((methylamino)methyl)pyrimidin-4-yloxy)-N-(5-(1-(trifluoromethyl)cyclopropyl)isoxazol-3-yl)-1H-indole-1-carboxamide;

N-(1-isopropyl-5-methyl-1H-pyrazol-3-yl)-5-(6-((methylamino)methyl)pyrimidin-4-yloxy)-1H-indole-1-carboxamide;

(S)—N-(5-cyclopropylisoxazol-3-yl)-5-(6-methyl-7-(2-(methylamino)-2-oxoethyl)-5,6,7,8-tetrahydropyrido[3,4-d]pyrimidin-4-yloxy)-1H-indole-1-carboxamide;

(S)—N-(5-cyclopropylisoxazol-3-yl)-5-(7-isopropyl-6-methyl-5,6,7,8-tetrahydropyrido[3,4-d]pyrimidin-4-yloxy)-1H-indole-1-carboxamide;

(S)—N-(5-cyclopropylisoxazol-3-yl)-5-(6-methyl-7-propyl-5,6,7,8-tetrahydropyrido[3,4-d]pyrimidin-4-yloxy)-1H-indole-1-carboxamide;

N-(1-tert-butyl-1H-pyrazol-3-yl)-5-(5,6,7,8-tetrahydropyrido[3,4-d]pyrimidin-4-yloxy)-1H-indole-1-carboxamide;

5-(6-(cyclopropanecarbonyl)-6,7-dihydro-5H-pyrrolo[3,4-d]pyrimidin-4-yloxy)-N-(5-isopropylisoxazol-3-yl)-1H-indole-1-carboxamide;

N-(5-isopropylisoxazol-3-yl)-5-(6-(2-methylpropanoyl)-6,7-dihydro-5H-pyrrolo[3,4-d]pyrimidin-4-yloxy)-1H-indole-1-carboxamide;

5-(6-(cyclopropanecarbonyl)-6,7-dihydro-5H-pyrrolo[3,4-d]pyrimidin-4-yloxy)-N-(5-cyclopropylisoxazol-3-yl)-1H-indole-1-carboxamide;

N-(5-cyclopropylisoxazol-3-yl)-5-(6-(2-methylpropanoyl)-6,7-dihydro-5H-pyrrolo[3,4-d]pyrimidin-4-yloxy)-1H-indole-1-carboxamide;

5-(6-(cyclopropanecarbonyl)-6,7-dihydro-5H-pyrrolo[3,4-d]pyrimidin-4-yloxy)-N-(5-(1-methylcyclopropyl)isoxazol-3-yl)-1H-indole-1-carboxamide;

N-(5-(1-methylcyclopropyl)isoxazol-3-yl)-5-(6-(2-methylpropanoyl)-6,7-dihydro-5H-pyrrolo[3,4-d]pyrimidin-4-yloxy)-1H-indole-1-carboxamide;

(S)—N-(5-cyclopropylisoxazol-3-yl)-5-(6-methyl-7-(2-methylpropanoyl)-5,6,7,8-tetrahydropyrido[3,4-d]pyrimidin-4-yloxy)-1H-indole-1-carboxamide;

(S)—N-(5-cyclopropylisoxazol-3-yl)-5-(6-methyl-7-(3-methylbutanoyl)-5,6,7,8-tetrahydropyrido[3,4-d]pyrimidin-4-yloxy)-1H-indole-1-carboxamide;

(S)-4-(1-(5-cyclopropylisoxazol-3-ylcarbamoyl)-1H-indol-5-yloxy)-N-ethyl-6-methyl-5,6-dihydropyrido[3,4-d]pyrimidine-7(8H)-carboxamide;

(S)—N-(5,6-dihydro-4H-pyrrolo[1,2-b]pyrazol-2-yl)-5-(7-ethanoyl-6-methyl-5,6,7,8-tetrahydropyrido[3,4-d]pyrimidin-4-yloxy)-1H-indole-1-carboxamide;

(R)—N-(5-cyclopropylisoxazol-3-yl)-5-(6-methyl-5,6,7,8-tetrahydropyrido[3,4-d]pyrimidin-4-yloxy)-1H-indole-1-carboxamide;

(S)-5-(7-butyl-6-methyl-5,6,7,8-tetrahydropyrido[3,4-d]pyrimidin-4-yloxy)-N-(5-cyclopropylisoxazol-3-yl)-1H-indole-1-carboxamide;

(S)—N-(5-cyclopropylisoxazol-3-yl)-5-(7-isopentyl-6-methyl-5,6,7,8-tetrahydropyrido[3,4-d]pyrimidin-4-yloxy)-1H-indole-1-carboxamide;

(R)—N-(5-cyclopropylisoxazol-3-yl)-5-(7-ethanoyl-6-methyl-5,6,7,8-tetrahydropyrido[3,4-d]pyrimidin-4-yloxy)-1H-indole-1-carboxamide;

(S)-5-(6-methyl-7-propyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

(S)—N-(5-cyclopropylisoxazol-3-yl)-5-(6-methyl-7-propanoyl-5,6,7,8-tetrahydropyrido[3,4-d]pyrimidin-4-yloxy)-1H-indole-1-carboxamide;

(S)-5-(7-butanoyl-6-methyl-5,6,7,8-tetrahydropyrido[3,4-d]pyrimidin-4-yloxy)-N-(5-cyclopropylisoxazol-3-yl)-1H-indole-1-carboxamide;

(S)-5-(6,7-dimethyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

5-(8-ethyl-6,7,8,9-tetrahydro-5H-pyrimido[4,5-c]azepin-4-yloxy)-N-(5-(1-(trifluoromethyl)cyclopropyl)isoxazol-3-yl)-1H-indole-1-carboxamide;1

(S)-5-(7-ethanoyl-6-methyl-5,6,7,8-tetrahydropyrido[3,4-d]pyrimidin-4-yloxy)-N-(5-isopropylisoxazol-3-yl)-1H-indole-1-carboxamide;

(S)-4-methyl-5-(6-methyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

(S)-5-(7-(cyclobutanecarbonyl)-6-methyl-5,6,7,8-tetrahydropyrido[3,4-d]pyrimidin-4-yloxy)-N-(5-cyclopropylisoxazol-3-yl)-1H-indole-1-carboxamide;

(S)—N-(5-cyclopropylisoxazol-3-yl)-4-methyl-5-(6-methyl-5,6,7,8-tetrahydropyrido[3,4-d]pyrimidin-4-yloxy)-1H-indole-1-carboxamide;

(S)-5-(7-ethanoyl-6-methyl-5,6,7,8-tetrahydropyrido[3,4-d]pyrimidin-4-yloxy)-N-(5-isopropylisoxazol-3-yl)-4-methyl-1H-indole-1-carboxamide;

(S)-5-(7-ethanoyl-6-methyl-5,6,7,8-tetrahydropyrido[3,4-d]pyrimidin-4-yloxy)-4-methyl-N-(5-(1-methylcyclopropyl)isoxazol-3-yl)-1H-indole-1-carboxamide;

(S)-5-(7-ethanoyl-6-methyl-5,6,7,8-tetrahydropyrido[3,4-d]pyrimidin-4-yloxy)-4-methyl-N-(5-(1-(trifluoromethyl)cyclopropyl)isoxazol-3-yl)-1H-indole-1-carboxamide;

(S)-5-(7-ethanoyl-6-methyl-5,6,7,8-tetrahydropyrido[3,4-d]pyrimidin-4-yloxy)-N-(5-methylisoxazol-3-yl)-1H-indole-1-carboxamide;

(S)—N-(5-isopropylisoxazol-3-yl)-4-methyl-5-(6-methyl-5,6,7,8-tetrahydropyrido[3,4-d]pyrimidin-4-yloxy)-1H-indole-1-carboxamide;

(S)-4-methyl-5-(6-methyl-5,6,7,8-tetrahydropyrido[3,4-d]pyrimidin-4-yloxy)-N-(5-(1-methylcyclopropyl)isoxazol-3-yl)-1H-indole-1-carboxamide;

(S)—N-(1-tert-butyl-1H-pyrazol-3-yl)-5-(6-methyl-5,6,7,8-tetrahydropyrido[3,4-d]pyrimidin-4-yloxy)-1H-indole-1-carboxamide;

5-(6-ethanoyl-6,7-dihydro-5H-pyrrolo[3,4-d]pyrimidin-4-yloxy)-4-methyl-N-(5-(1-methylcyclopropyl)isoxazol-3-yl)-1H-indole-1-carboxamide;

(S)-5-(7-ethanoyl-6-methyl-5,6,7,8-tetrahydropyrido[3,4-d]pyrimidin-4-yloxy)-N-(3-(trifluoromethyl)phenyl)-1H-indole-1-carboxamide;

(S)—N-(5-cyclopropylisoxazol-3-yl)-5-(7-ethanoyl-6-methyl-5,6,7,8-tetrahydropyrido[3,4-d]pyrimidin-4-yloxy)-4-methyl-1H-indole-1-carboxamide;

5-(6-ethanoyl-6,7-dihydro-5H-pyrrolo[3,4-d]pyrimidin-4-yloxy)-4-methyl-N-(5-(1-(trifluoromethyl)cyclopropyl)isoxazol-3-yl)-1H-indole-1-carboxamide;

(S)—N-(1-tert-butyl-1H-pyrazol-3-yl)-5-(7-ethanoyl-6-methyl-5,6,7,8-tetrahydropyrido[3,4-d]pyrimidin-4-yloxy)-1H-indole-1-carboxamide;

N-(5-cyclopropyl-1H-pyrazol-3-yl)-5-(6-((methylamino)methyl)pyrimidin-4-yloxy)-1H-indole-1-carboxamide;

N-(5-cyclopropylisoxazol-3-yl)-5-(6-ethanoyl-6,7-dihydro-5H-pyrrolo[3,4-d]pyrimidin-4-yloxy)-4-methyl-1H-indole-1-carboxamide;

N-(1-tert-butyl-1H-pyrazol-3-yl)-5-(6,7-dihydro-5H-pyrrolo[3,4-d]pyrimidin-4-yloxy)-1H-indole-1-carboxamide;

N-(1-tert-butyl-1H-pyrazol-3-yl)-5-(6-((methylamino)methyl)pyrimidin-4-yloxy)-1H-indole-1-carboxamide;

5-(6-((ethylamino)methyl)pyrimidin-4-yloxy)-N-(5-isopropyl-1H-pyrazol-3-yl)-1H-indole-1-carboxamide;

5-(6-(2-(dimethylamino)ethyl)pyrimidin-4-yloxy)-N-(5-isopropyl-1H-pyrazol-3-yl)-1H-indole-1-carboxamide;

N-(5-cyclopropyl-1-methyl-1H-pyrazol-3-yl)-5-(6-((methylamino)methyl)pyrimidin-4-yloxy)-1H-indole-1-carboxamide;

N-(1-methyl-5-(trifluoromethyl)-1H-pyrazol-3-yl)-5-(6-((methylamino)methyl)pyrimidin-4-yloxy)-1H-indole-1-carboxamide N-(5-methyl-1-(2,2,2-trifluoroethyl)-1H-pyrazol-3-yl)-5-(6-((methylamino)methyl)pyrimidin-4-yloxy)-1H-indole-1-carboxamide;

5-(6,7-dihydro-5H-pyrrolo[3,4-d]pyrimidin-4-yloxy)-N-(1-methyl-5-(trifluoromethyl)-1H-pyrazol-3-yl)-1H-indole-1-carboxamide;

(S)-5-(6-methyl-5,6,7,8-tetrahydropyrido[3,4-d]pyrimidin-4-yloxy)-N-(1-methyl-5-(trifluoromethyl)-1H-pyrazol-3-yl)-1H-indole-1-carboxamide;

5-(5,7-dihydrothieno[3,4-d]pyrimidin-4-yloxy)-N-(1-methyl-5-(trifluoromethyl)-1H-pyrazol-3-yl)-1H-indole-1-carboxamide;

(S)-5-(7-ethanoyl-6-methyl-5,6,7,8-tetrahydropyrido[3,4-d]pyrimidin-4-yloxy)-N-(1-ethyl-1H-pyrazol-3-yl)-1H-indole-1-carboxamide;

(S)-5-(7-ethanoyl-6-methyl-5,6,7,8-tetrahydropyrido[3,4-d]pyrimidin-4-yloxy)-N-(1-ethyl-5-methyl-1H-pyrazol-3-yl)-1H-indole-1-carboxamide;

(S)—N-(1-cyclopropyl-5-methyl-1H-pyrazol-3-yl)-5-(7-ethanoyl-6-methyl-5,6,7,8-tetrahydropyrido[3,4-d]pyrimidin-4-yloxy)-1H-indole-1-carboxamide;

(S)—N-(1-cyclopropyl-1H-pyrazol-3-yl)-5-(7-ethanoyl-6-methyl-5,6,7,8-tetrahydropyrido[3,4-d]pyrimidin-4-yloxy)-1H-indole-1-carboxamide;

(S)-5-(7-ethanoyl-6-methyl-5,6,7,8-tetrahydropyrido[3,4-d]pyrimidin-4-yloxy)-N-(1-isopropyl-5-methyl-1H-pyrazol-3-yl)-1H-indole-1-carboxamide;

N-(5-cyclopropyl-1-methyl-1H-pyrazol-3-yl)-5-(6-ethanoyl-6,7-dihydro-5H-pyrrolo[3,4-d]pyrimidin-4-yloxy)-1H-indole-1-carboxamide;

5-(6-ethanoyl-6,7-dihydro-5H-pyrrolo[3,4-d]pyrimidin-4-yloxy)-N-(1-methyl-5-(trifluoromethyl)-1H-pyrazol-3-yl)-1H-indole-1-carboxamide;

(S)—N-(5-cyclopropyl-1-methyl-1H-pyrazol-3-yl)-5-(7-ethanoyl-6-methyl-5,6,7,8-tetrahydropyrido[3,4-d]pyrimidin-4-yloxy)-1H-indole-1-carboxamide;

(S)-5-(7-ethanoyl-6-methyl-5,6,7,8-tetrahydropyrido[3,4-d]pyrimidin-4-yloxy)-N-(1-methyl-5-(trifluoromethyl)-1H-pyrazol-3-yl)-1H-indole-1-carboxamide;

(S)-5-(7-ethanoyl-6-methyl-5,6,7,8-tetrahydropyrido[3,4-d]pyrimidin-4-yloxy)-N-(5-methyl-1-(2,2,2-trifluoroethyl)-1H-pyrazol-3-yl)-1H-indole-1-carboxamide;

N-(1-cyclopropyl-5-methyl-1H-pyrazol-3-yl)-5-(6,7-dihydro-5H-pyrrolo[3,4-d]pyrimidin-4-yloxy)-1H-indole-1-carboxamide;

(S)—N-(1-tert-butyl-5-methyl-1H-pyrazol-3-yl)-5-(6-methyl-5,6,7,8-tetrahydropyrido[3,4-d]pyrimidin-4-yloxy)-1H-indole-1-carboxamide;

N-(5-cyclopropyl-1H-pyrazol-3-yl)-4-methyl-5-(6-((methylamino)methyl)pyrimidin-4-yloxy)-1H-indole-1-carboxamide;

N-(5-cyclopropyl-1-methyl-1H-pyrazol-3-yl)-4-methyl-5-(6-((methylamino)methyl)pyrimidin-4-yloxy)-1H-indole-1-carboxamide;

4-methyl-N-(1-methyl-5-(trifluoromethyl)-1H-pyrazol-3-yl)-5-(6-((methylamino)methyl)pyrimidin-4-yloxy)-1H-indole-1-carboxamide;

(S)—N-(1,5-dimethyl-1H-pyrazol-3-yl)-5-(7-ethanoyl-6-methyl-5,6,7,8-tetrahydropyrido[3,4-d]pyrimidin-4-yloxy)-1H-indole-1-carboxamide;

(S)—N-(1-tert-butyl-5-methyl-1H-pyrazol-3-yl)-5-(7-ethanoyl-6-methyl-5,6,7,8-tetrahydropyrido[3,4-d]pyrimidin-4-yloxy)-1H-indole-1-carboxamide;

5-(6,7-dihydro-5H-pyrrolo[3,4-d]pyrimidin-4-yloxy)-N-(1-ethyl-5-methyl-1H-pyrazol-3-yl)-1H-indole-1-carboxamide;

N-(1-ethyl-5-methyl-1H-pyrazol-3-yl)-5-(6-((methylamino)methyl)pyrimidin-4-yloxy)-1H-indole-1-carboxamide;

N-(1-tert-butyl-5-methyl-1H-pyrazol-3-yl)-5-(6-((methylamino)methyl)pyrimidin-4-yloxy)-1H-indole-1-carboxamide;

N-(5-isopropyl-1-methyl-1H-pyrazol-3-yl)-5-(6-((methylamino)methyl)pyrimidin-4-yloxy)-1H-indole-1-carboxamide;

N-(1-ethyl-5-(trifluoromethyl)-1H-pyrazol-3-yl)-5-(6-((methylamino)methyl)pyrimidin-4-yloxy)-1H-indole-1-carboxamide;

N-(5-tert-butyl-1-methyl-1H-pyrazol-3-yl)-5-(6-((methylamino)methyl)pyrimidin-4-yloxy)-1H-indole-1-carboxamide;

(S)—N-(1-tert-butyl-1H-pyrazol-3-yl)-4-methyl-5-(6-methyl-5,6,7,8-tetrahydropyrido[3,4-d]pyrimidin-4-yloxy)-1H-indole-1-carboxamide;

N-(5-cyclopropyl-1-ethyl-1H-pyrazol-3-yl)-5-(6-((methylamino)methyl)pyrimidin-4-yloxy)-1H-indole-1-carboxamide;

(S)—N-(1-ethyl-5-(trifluoromethyl)-1H-pyrazol-3-yl)-4-methyl-5-(6-methyl-5,6,7,8-tetrahydropyrido[3,4-d]pyrimidin-4-yloxy)-1H-indole-1-carboxamide;

(S)—N-(1-ethyl-5-(trifluoromethyl)-1H-pyrazol-3-yl)-5-(6-methyl-5,6,7,8-tetrahydropyrido[3,4-d]pyrimidin-4-yloxy)-1H-indole-1-carboxamide;

(S)-5-(7-ethanoyl-6-methyl-5,6,7,8-tetrahydropyrido[3,4-d]pyrimidin-4-yloxy)-N-(1-ethyl-5-(trifluoromethyl)-1H-pyrazol-3-yl)-1H-indole-1-carboxamide;

(S)-5-(7-(cyclopropanecarbonyl)-6-methyl-5,6,7,8-tetrahydropyrido[3,4-d]pyrimidin-4-yloxy)-N-(5-cyclopropylisoxazol-3-yl)-4-methyl-1H-indole-1-carboxamide;

(S)-4-methyl-5-(6-methyl-5,6,7,8-tetrahydropyrido[3,4-d]pyrimidin-4-yloxy)-N-(1-methyl-5-(trifluoromethyl)-1H-pyrazol-3-yl)-1H-indole-1-carboxamide;

(S)-ethyl 4-(1-(5-cyclopropylisoxazol-3-ylcarbamoyl)-4-methyl-1H-indol-5-yloxy)-6-methyl-5,6-dihydropyrido[3,4-d]pyrimidine-7(8H)-carboxylate;

N-(1-methyl-5-(1-methylcyclopropyl)-1H-pyrazol-3-yl)-5-(6-((methylamino)methyl)pyrimidin-4-yloxy)-1H-indole-1-carboxamide;

(S)—N-(5-cyclopropylisoxazol-3-yl)-4-methyl-5-(6-methyl-7-propanoyl-5,6,7,8-tetrahydropyrido[3,4-d]pyrimidin-4-yloxy)-1H-indole-1-carboxamide;

(S)-5-(7-ethanoyl-6-methyl-5,6,7,8-tetrahydropyrido[3,4-d]pyrimidin-4-yloxy)-4-methyl-N-(1-methyl-5-(trifluoromethyl)-1H-pyrazol-3-yl)-1H-indole-1-carboxamide;

(S)-5-(7-ethanoyl-6-methyl-5,6,7,8-tetrahydropyrido[3,4-d]pyrimidin-4-yloxy)-N-(1-ethyl-5-(trifluoromethyl)-1H-pyrazol-3-yl)-4-methyl-1H-indole-1-carboxamide;

N-(5-cyclopropyl-1-methyl-1H-pyrazol-3-yl)-5-(2-((methylamino)methyl)pyridin-4-yloxy)-1H-indole-1-carboxamide;

N-(1-cyclopropyl-5-methyl-1H-pyrazol-3-yl)-5-(6-((methylamino)methyl)pyrimidin-4-yloxy)-1H-indole-1-carboxamide;

N-(1,5-dicyclopropyl-1H-pyrazol-3-yl)-5-(6-((methylamino)methyl)pyrimidin-4-yloxy)-1H-indole-1-carboxamide;

N-(1-methyl-5-(trifluoromethyl)-1H-pyrazol-3-yl)-5-(2-((methylamino)methyl)pyridin-4-yloxy)-1H-indole-1-carboxamide;

(S)-5-(7-(cyclopropanecarbonyl)-6-methyl-5,6,7,8-tetrahydropyrido[3,4-d]pyrimidin-4-yloxy)-N-(1-methyl-5-(trifluoromethyl)-1H-pyrazol-3-yl)-1H-indole-1-carboxamide;

N-(5-cyclopropyl-1-isopropyl-1H-pyrazol-3-yl)-5-(6-((methylamino)methyl)pyrimidin-4-yloxy)-1H-indole-1-carboxamide;

(S)—N-(5-cyclopropyl-1-isopropyl-1H-pyrazol-3-yl)-5-(6-methyl-5,6,7,8-tetrahydropyrido[3,4-d]pyrimidin-4-yloxy)-1H-indole-1-carboxamide;

(S)—N-(5-cyclopropyl-1-isopropyl-1H-pyrazol-3-yl)-5-(7-ethanoyl-6-methyl-5,6,7,8-tetrahydropyrido[3,4-d]pyrimidin-4-yloxy)-1H-indole-1-carboxamide;

N-(1-cyclopropyl-5-ethyl-1H-pyrazol-3-yl)-5-(6-((methylamino)methyl)pyrimidin-4-yloxy)-1H-indole-1-carboxamide;

(S)-ethyl 6-methyl-4-(1-(5-(1-(trifluoromethyl)cyclopropyl)isoxazol-3-ylcarbamoyl)-1H-indol-5-yloxy)-5,6-dihydropyrido[3,4-d]pyrimidine-7(8H)-carboxylate;

(S)-ethyl 4-(1-(5-cyclopropylisoxazol-3-ylcarbamoyl)-1H-indol-5-yloxy)-6-methyl-5,6-dihydropyrido[3,4-d]pyrimidine-7(8H)-carboxylate;

(S)-methyl 6-methyl-4-(1-(5-(1-(trifluoromethyl)cyclopropyl)isoxazol-3-ylcarbamoyl)-1H-indol-5-yloxy)-5,6-dihydropyrido[3,4-d]pyrimidine-7(8H)-carboxylate;

N-(1-methyl-5-(trifluoromethyl)-1H-pyrazol-3-yl)-5-(6-(methylsulfonylmethyl)pyrimidin-4-yloxy)-1H-indole-1-carboxamide;

5-(6-(aminomethyl)pyrimidin-4-yloxy)-N-(1-methyl-5-(trifluoromethyl)-1H-pyrazol-3-yl)-1H-indole-1-carboxamide;

(S)—N-(1-cyclopropyl-5-ethyl-1H-pyrazol-3-yl)-5-(7-ethanoyl-6-methyl-5,6,7,8-tetrahydropyrido[3,4-d]pyrimidin-4-yloxy)-1H-indole-1-carboxamide;

(S)—N-(1,5-dicyclopropyl-1H-pyrazol-3-yl)-5-(6-methyl-5,6,7,8-tetrahydropyrido[3,4-d]pyrimidin-4-yloxy)-1H-indole-1-carboxamide 5-(6-(aminomethyl)pyrimidin-4-yloxy)-N-(5-cyclopropyl-1-methyl-1H-pyrazol-3-yl)-1H-indole-1-carboxamide;

N-(5-cyclopropyl-1-methyl-1H-pyrazol-3-yl)-5-(6-((ethylamino)methyl)pyrimidin-4-yloxy)-1H-indole-1-carboxamide; and (S)—N-(1,5-dicyclopropyl-1H-pyrazol-3-yl)-5-(7-ethanoyl-6-methyl-5,6,7,8-tetrahydropyrido[3,4-d]pyrimidin-4-yloxy)-1H-indole-1-carboxamide;

One highly preferred 1H-indole-1-carboxamide is N-(1-methyl-5-(trifluoromethyl)-1H-pyrazol-3-yl)-5-((6-((methylamino)methyl)pyrimidin-4-yl)oxy)-1H-indole-1-carboxamide. The structure of this 1H-indole-1-carboxamide is shown below:

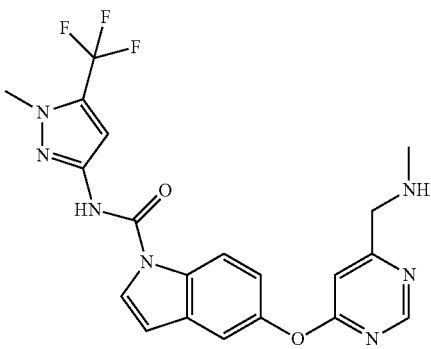

It is to be understood that the ophthalmic composition of the present invention can include any one or any combination of two, three, four or more of the 1H-indole-1-carboxamides discussed herein The 1H-indole-1-carboxamide may be added to the composition in its native form or a salt form. Suitable salt forms include, without limitation, hydrochloride salt, sulfate salt, phosphate salt, acetate salt or citrate salt of the 1H-indole-1-carboxamide or combinations thereof. It has been found that the hydrochloride salt of the 1H-indole-1-carboxamide is highly desirable.

The concentration of 1H-indole-1-carboxamide, particularly N-(1-methyl-5-(trifluoromethyl)-1H-pyrazol-3-yl)-5-((6-((methylamino)methyl)pyrimidin-4-yl)oxy)-1H-indole-1-carboxamide, in the composition of the present invention is typically greater than about 0.1 w/v %, more typically greater than about 0.4 w/v %, even more typically greater than about 1.0 w/v % and potentially greater than about 1.8 w/v % and even possibly greater than 2.5 w/v %. Moreover, the concentration of 1H-indole-1-carboxamide, particularly N-(1-methyl-5-(trifluoromethyl)-1H-pyrazol-3-yl)-5-((6-((methylamino)methyl)pyrimidin-4-yl)oxy)-1H-indole-1-carboxamide, in the composition is typically less about 5.0 w/v %, more typically less than about 4.0 w/v % and even more typically less than about 3.3 w/v % and even possibly less than about 2.3 w/v %. It is specifically contemplated that any of the lower limits on the concentration of 1H-indole-1-carboxamide may be used in conjunction with any of the upper limits on the concentrations of 1H-indole-1-carboxamide. Preferred ranges for the concentration of 1H-indole-1-carboxamide, particularly N-(1-methyl-5-(trifluoromethyl)-1H-pyrazol-3-yl)-5-((6-((methylamino)methyl)pyrimidin-4-yl)oxy)-1H-indole-1-carboxamide, in the composition are as follows: greater than about 0.4 w/v % but less than about 4.0 w/v %; greater than about 0.4 w/v % but less than about 3.3 w/v %; greater than about 1.8 w/v % but less than about 4.0 w/v %; and greater than about 1.8 w/v % but less than about 3.3 w/v %. The concentrations of 1H-indole-1-carboxamide herein refer to the concentration of the 1H-indole-1-carboxamide only and do not take into account the weight or concentration of the salt of the 1H-indole-1-carboxamide where the 1H-indole-1-carboxamide is provided in salt form within the composition.

The average particle size of 1H-indole-1-carboxamide, particularly N-(1-methyl-5-(trifluoromethyl)-1H-pyrazol-3-yl)-5-((6-((methylamino)methyl)pyrimidin-4-yl)oxy)-1H-indole-1-carboxamide, in the composition of the present invention is typically at least about 0.01 micron more typically at least about 0.2 micron, even more typically at least about 0.5 micron and potentially greater than about 1.0 micron. Moreover, the average particle size of the 1H-indole-1-carboxamide, particularly N-(1-methyl-5-(trifluoromethyl)-1H-pyrazol-3-yl)-5-((6-((methylamino)methyl)pyrimidin-4-yl)oxy)-1H-indole-1-carboxamide, in the composition is typically no greater than about 5.0 microns, more typically no greater than about 3.0 microns and even more typically no greater than about 2.0 microns. It is specifically contemplated that any of the lower limits on the concentration of 1H-indole-1-carboxamide may be used in conjunction with any of the upper limits on the concentrations of 1H-indole-1-carboxamide. Preferred ranges for the concentration of 1H-indole-1-carboxamide, particularly N-(1-methyl-5-(trifluoromethyl)-1H-pyrazol-3-yl)-5 #6-((methylamino)methyl)pyrimidin-4-yl)oxy)-1H-indole-1-carboxamide, in the composition are as follows: at least about 0.01 microns but no greater than about 5.0 microns; at least about 0.2 micron but no greater than about 3.0 microns; at least about 0.5 micron but less than about 2.0 microns. Particle size for the suspensions was measured using laser light scattering techniques performed by a Microtrac Blue-wave instrument.

The ophthalmic composition containing the 1H-indole-carboxamide may be used alone to treat an ophthalmic condition or disease or may be used in conjunction with other drugs or other treatments. Examples of other drugs or treatments include, without limitation, MACUGEN®, VEGF trap (EYLEA®), photodynamic therapy, anecortave acetate, steroids, non-steroidal anti-inflammatory (e.g. naproxen, ibuprofen, diclofenac) Cox-1 and Cox-2 inhibitors, cyclosporine, dexamethasone, mTOR (mammalian target of rapamycin) inhibitors such as rapamycin, everolimus, and the like, PKC (protein kinase C) beta inhibitors, tumor necrosis alpha inhibitors, interleukin one beta inhibitors, platelet derived growth factor (PDGF) beta and alpha and receptors inhibitors, anti-PDGF antibodies, anti-PDGFR antibodies, anti-PDGF apatemers, LUCENTIS®, AVASTIN®, VEGF antibodies, PLGF antibodies, VEGF scFv's, siRNA against VEGF family (A-E, PLGF, neuropilin)/VEGF receptors, complement inhibitors targeting classical, alternative and lectin pathways, IL-10 inhibitors, C5aR inhibitors, C3aR inhibitors, and inhibitors of sphingosine phosphate and receptors.

The composition of the present invention typically includes a preservative. Potential preservatives include, without limitation, hydrogen peroxide, polyhexylmethylene biguanidine (PHMB), polymeric quaternary ammonium compound (e.g., polyquaternium-1), chlorine containing preservatives such as benzalkonium chloride (BAK), chlorite preservatives or others. The composition of the invention may also be self-preserved and may be without a preservative.

The polymeric quaternary ammonium compounds useful in the composition of the present invention are those which have an antimicrobial effect and which are ophthalmically acceptable. Preferred compounds of this type are described in U.S. Pat. Nos. 3,931,319; 4,027,020; 4,407,791; 4,525,346; 4,836,986; 5,037,647 and 5,300,287; and PCT application WO 91/09523 (Dziabo et al.). The most preferred polymeric ammonium compound is polyquaternium 1, otherwise known as POLYQUAD® or ONAMERM® with a number average molecular weight between 2,000 to 30,000. Preferably, the number average molecular weight is between 3,000 to 14,000.

When used, the polymeric quaternary ammonium compound is generally used in the composition of the present invention in an amount that is greater than about 0.00001 w/v %, more typically greater than about 0.0003 w/v % and even more typically greater than about 0.0007 w/v % of the ophthalmic composition. Moreover, the polymeric quaternary ammonium compound, when used in the composition, of the present invention, is generally used at a concentration that is less than about 0.03 w/v %, more typically less than about 0.003 w/v % and even more typically less than about 0.0015 w/v % of the ophthalmic composition. It is specifically contemplated that any of the lower limits on the concentration of polymeric quaternary ammonium compound may be used in conjunction with any of the upper limits on the concentrations of polymeric quaternary ammonium compound. Preferred ranges for the concentration of polymeric quaternary ammonium compound in the composition are as follows: greater than about 0.0003 w/v % but less than about 0.003 w/v %; greater than about 0.0003 w/v % but less than about 0.0015 w/v %; greater than about 0.0007 w/v % but less than about 0.003 w/v %; and greater than about 0.0007 w/v % but less than about 0.0015 w/v %.

When used, BAK is typically in the composition at a concentration that is at least 0.0005 w/v %, more typically greater than about 0.001 w/v % and even possibly greater than about 0.007 w/v % of the ophthalmic composition. Moreover, BAK, when used in the composition, is generally used at a concentration that is less than about 0.1 w/v %, more typically less than about 0.02 w/v % and even possibly less than about 0.0035 w/v % of the ophthalmic composition. It is specifically contemplated that any of the lower limits on the concentration of BAK may be used in conjunction with any of the upper limits on the concentrations of BAK. Preferred ranges for the concentration of BAK in the composition are as follows: greater than about 0.001 w/v % but less than about 0.02 w/v %; greater than about 0.001 w/v % but less than about 0.0035 w/v %; greater than about 0.007 w/v % but less than about 0.02 w/v %; and greater than about 0.007 w/v % but less than about 0.0035 w/v %.

As suggested previously, the ophthalmic composition can include one or more polyols. Generally, these polyols, in conjunction with borate, can enhance preservation of the composition.

In a preferred embodiment, the composition includes a polyol aptly described as a sugar alcohol that includes an alkyl chain with hydroxyl group (—OH groups) attached to a substantial portion (i.e., greater than 50, 70 or 90 percent or all) of the carbons in the alkyl chain. The alkyl chains of this polyol typically include 5 carbons (pentane), 6 carbons (hexane), 7 carbons (heptane) or any combination thereof. Examples of suitable polyols falling under this category include, without limitation, mannitol ((2R,3R,4R,5R)-hexane-1,2,3,4,5,6-hexyl), sorbitol ((2R,3S,4S,5 S)-hexane-1,2,3,4,5,6-hexyl), combinations thereof or the like. Another such polyol is xylitol ((2R,4S)-pentane-1,2,3,4,5-pentaol). When included, this type of polyol is typically at least about 0.01 w/v %, more typically at least about 0.15 w/v % and even more typically at least about 0.25 w/v % of the ophthalmic composition. This type of polyol is also typically less than about 5 w/v %, more typically less than about 1.6 w/v % and even more typically less than about 0.5 w/v % of the ophthalmic composition. It is specifically contemplated that any of the lower limits on the concentration of this type of polyol may be used in conjunction with any of the upper limits on the concentration of this type of polyol. Preferred ranges for the concentration of this type of polyol in the composition are as follows: greater than about 0.15 w/v % but less than about 1.6 w/v %; greater than about 0.15 w/v % but less than about 0.5 w/v %; greater than about 0.25 w/v % but less than about 1.6 w/v %; and greater than about 0.25 w/v % but less than about 0.5 w/v %.

Additionally or alternatively, the composition will include a polyol that is also a sugar alcohol that includes an alkyl chain with hydroxyl group (—OH groups) attached to a substantial portion (i.e., greater than 50, 70 or 90 percent or all) of the carbons in the alkyl chain. However, the alkyl chains of this alternative or additional polyol typically includes 2 carbons (ethane), 3 carbons (propane) or 4 carbons (butane). Examples of such polyols include, without limitation, glycerol (propane-1,2,3-triol), propylene glycol (propane-1,2-diol), combinations thereof or the like. When included, the concentration of this type of polyol is typically at least about 0.015 w/v %, more typically at least about 0.2 w/v % and even more typically at least about 0.5 w/v % of the ophthalmic composition. When included, this type of polyol is also typically less than about 7 w/v %, more typically less than about 5 w/v %, even more typically less than about 1.8 w/v % and even more typically less than about 1.2 w/v % of the ophthalmic composition. It is specifically contemplated that any of the lower limits on the concentration of this type of polyol may be used in conjunction with any of the upper limits on the concentration of this type of polyol. Preferred ranges for the concentration of this type of polyol in the composition are as follows: greater than about 0.2 w/v % but less than about 1.8 w/v %; greater than about 0.2 w/v % but less than about 1.2 w/v %; greater than about 0.5 w/v % but less than about 1.8 w/v %; and greater than about 0.5 w/v % but less than about 1.2 w/v %.

Borate, particularly boric acid, is a highly preferred buffering agent for the composition of the present invention. Typically, for the present invention, the concentration of borate in the composition is at least about 0.05 w/v %, more typically at least about 0.1 w/v % and still more typically at least about 0.25 w/v % of the ophthalmic composition. Furthermore, the concentration of borate in the composition is typically less than about 1.5 w/v %, more typically less than about 0.8 w/v % and still more typically less than about 0.4 w/v %, and even possibly less than about 0.35 w/v % of the ophthalmic composition. It is specifically contemplated that any of the lower limits on the concentration of borate may be used in conjunction with any of the upper limits on the concentration of borate. Preferred ranges for the concentration of borate in the composition are as follows: greater than about 0.1 w/v % but less than about 0.8 w/v %; greater than about 0.1 w/v % but less than about 0.4 w/v %; greater than about 0.25 w/v % but less than about 0.8 w/v %; and greater than about 0.25 w/v % but less than about 0.4 w/v %.

The composition of the present invention can additionally include any combination of the followings ingredients: one or more surfactant[s] (e.g., polysorbate, tyloxapol, polyethoxylated castor oil, combinations thereof or the like), one or more viscosity agent[s] (e.g., cellulosic polymer, galactomannan polymer, carboxyvinyl polymer, combinations thereof or the like); one or more tonicity agent[s] (e.g., sodium chloride), or other suitable ingredients. Tyloxapol is a preferred surfactant and, when included, is in the composition at a concentration that is at least about 0.009 w/v % but no greater than about 0.1 w/v %. Sodium chloride is a preferred osmolality agent and, when included, is in the composition at a concentration that is at least about 0.05 w/v % but no greater than about 1.5 w/v %.

The multi-dose ophthalmic composition of the present invention will typically exhibit sufficient antimicrobial activity to allow the compositions to satisfy the USP preservative efficacy requirements, as well as other preservative efficacy standards for is aqueous pharmaceutical compositions.

The preservative efficacy standards for multi-dose ophthalmic solutions in the U.S. and other countries/regions are set forth in the following table:

| | Preservative Efficacy Test ("PET") Criteria (Log Order Reduction of Microbial Inoculum Over Time) | |
|---|---|---|
| | Bacteria | Yeast and Molds (Fungi) |
| USP 36 | A reduction of 1 log (90%), 3 logs (99.9%) by day 14; and no increase after day 14 count | No increase (0.5 logs or greater relative to initial inoculum) from the initial calculated count at 7, 14 and 28 days. |
| Japan | 3 logs by 14 days; and no increase from day 14 through day 28. | No increase from initial count at 14 and 28 days |
| Ph. Eur. A[1] | A reduction of 2 logs (99%) by 6 hours; 3 logs by 24 hours; and no recovery after 28 days. | A reduction of 2 logs (99%) by 7 days, and no increase thereafter. |
| Ph. Eur. B | A reduction of 1 log at 24 hours; 3 logs by day 7; and no increase thereafter | A reduction of 1 log (90%) by day 14, and no increase thereafter. |
| FDA/ISO 14730 | A reduction of 3 logs from initial challenge at day 14; and a reduction of 3 logs from rechallenge | No increase higher than the initial value at day 14, and no increase higher than the day 14 rechallenge count through day 28. |

[1]There are two preservative efficacy standards in the European Pharmacopoeia ' "A" and "B".

Test microorganisms from compendia are: *Escherichia coli* (ATCC No. 8739), *Pseudomonas aeruginosa* (ATCC No. 9027), *Staphylococcus aureus* (ATCC No. 6538), *Candida albicans* (ATCC No. 10231) and *Aspergillus niger* (ATCC No. 16404). European Pharmacopoeia refers *Aspergillus niger* with new ACTT adopted name as *Aspergillus brasiliensis*.

The ophthalmic composition of the present invention is formulated so as to be compatible with the eye and/or other tissues to be treated with the compositions. For topical application to the eye, the composition of the present invention will generally be formulated as a sterile aqueous composition (e.g., suspensions, solutions, emulsions or the like) and typically include at least 70 w/v %, more typically 80 w/v % and even more typically at least 90 or 95 w/v % purified water. The ophthalmic composition is intended for direct application to the corneal surface of the eye and will typically be formulated so as to have a pH and tonicity that are compatible with the eye. The compositions will typically have a pH in the range of 4 to 9, preferably 5.5 to 8.5, and most preferably 5.5 to 8.0. Particularly desired pH ranges are 6.0 to 7.8 and more specifically 6.4 to 7.6. The compositions will typically have an osmolality of 200 to 400 or 450 milliosmoles per kilogram (mOsm/kg), more preferably 240 to 360 mOsm/kg. Further, the ophthalmic compositions suitable for multi-dose topical application are often disposed in a dispenser (preferably an eye dropper), which can dispense the ophthalmic composition (preferably as individual drops) to the corneal surface of the eye.

In one particularly preferred embodiment, the ophthalmic composition of the present invention is a suspension that includes a suspending agent for suspending the 1H-indole-1-carboxamide. Generally, it is contemplated that a variety of suspending agents such as carboxyvinyl polymer (e.g., carbomer), polysaccharide (e.g., xanthan gum) or others may be used to suspend the 1H-indole-1-carboxamide. Quite surprisingly, however, it has been found that cellulose, particularly substituted cellulose (i.e., cellulose derivative), is a highly desirable suspending agent for suspending the 1H-indole-1-carboxamide. In particular, and as further described below, it has been found that cellulose and cellulose derivatives can provide desirable suspension of the 1H-indole-1-carboxamide while avoiding negative effects encountered when other, more common suspending agents, are used to suspend the 1H-indole-1-carboxamide.

Examples of suitable substituted cellulose derivatives that can be used as suspending agents include, without limitation, methyl cellulose (MC), ethyl cellulose (EC), methyl ethyl cellulose (MEC), hydroxypropyl cellulose (HPC), hydroxyethyl cellulose (HEC), hydroxyethylmethyl cellulose (HEMC), hydroxypropylmethyl cellulose (HPMC), ethylhydroxyethyl cellulose (EHEC), combinations therefor or the like. When used as a suspending agent, the cellulose, cellulose derivative or combination thereof is in the composition at a concentration that is at least about 0.05 w/v %, more typically at least about 0.1 w/v % and still more typically at least about 0.25 w/v % of the ophthalmic composition. Furthermore, the concentration of cellulose, cellulose derivative or combination thereof in the composition is typically less than about 1.8 w/v %, more typically less than about 1.0 w/v % and still more typically less than about 0.8 w/v %, and even possibly less than about 0.6 w/v % of the ophthalmic composition. It is specifically contemplated that any of the lower limits on the concentration of cellulose, cellulose derivative or a combination thereof may be used in conjunction with any of the upper limits on the concentration of cellulose or cellulose derivative or a combination thereof. Preferred ranges for the concentration of cellulose, cellulose derivative or combination thereof in the composition are as follows: at least about 0.1 w/v % but less than about 0.8 w/v %; at least about 0.1 w/v % but less than about 0.6 w/v %; at least about 0.25 w/v % but less than about 0.8 w/v %; and at least about 0.25 w/v % but less than about 0.6 w/v %.

HEC is a highly preferred cellulosic derivative for use as suspending agent for suspending the 1H-indole-1-carboxamide. In at least one preferred embodiment, HEC is the sole suspending agent and sole cellulose derivative in the composition. When used as a suspending agent, HEC is in the composition at a concentration that is at least about 0.1 w/v %, more typically at least about 0.25 w/v % and still more typically at least about 0.35 w/v %. Furthermore, the concentration of HEC in the composition is typically less than about 1.0 w/v %, more typically less than about 0.7 w/v % and still more typically less than about 0.5 w/v %. It is specifically contemplated that any of the lower limits on the concentration of HEC may be used in conjunction with any of the upper limits on the concentration of HEC. Preferred ranges for the concentration of HEC in the composition are as follows: at least about 0.25 w/v % but less than about 0.7 w/v %; greater than about 0.25 w/v % but less than about 0.5 w/v %; greater than about 0.35 w/v % but less than about 0.7 w/v %; and greater than about 0.35 w/v % but less than about 0.5 w/v %. The weight average molecular weight of the HEC is typically from about 50,000 to about 2,000,000, more typically from about 250,000 to about 1,500,000, even more typically from about 700,000 to about 1,300,000 and still more typically from about 900,000 to about 1,100,000.

Advantageously, the cellulose, cellulose derivative or combination thereof, particularly HEC, can provide for desired viscosity of the composition while using relatively low concentrations thereof. Preferred formulation viscosity is from 2 to 100 cps, more preferred is from 5 to 75 cps, and most preferred is from 10-60 cps. Target viscosity can also provide for relative ease of manufacturing.

While cellulose derivative, particularly HEC, has been found to be a highly desirable suspending agent for the 1H-indole-1-carboxamide, it has been found that the 1H-indole-1-carboxamide has a strong tendency to agglomerate over time, particularly at elevated temperature, within the topical aqueous ophthalmic suspension even when suspended with HEC. Through extensive investigation, however, it has also been found that low molecular weight charged polymer, particularly cellulosic polymer, can ameliorate this tendency to agglomerate. As used herein, the phrase "low molecular weight" as it is used to describe polymers of the polymeric material means that those polymers of the polymeric material cooperatively have an average molecular weight that is less than 500,000, more typically less than 200,000 and even possibly less than 100,000 daltons (Da). The molecular weight will still typically be greater than 20,000 or even 50,000 daltons. Such polymers can be charged when they are in salt form. Particularly desirable cellulose polymers are salts of carboxymethyl cellulose (CMC) polymer such as sodium carboxymethyl cellulose (NaCMC). Sodium carboxymethyl cellulose suitable for use in the present invention has a degree of substitution (DS) of at least 0.2 and preferably at least about 0.5. The degree of substitution of the sodium carboxymethyl cellulose can be up to about 2.5, preferably up to about 0.9. The degree of polymerization (DP) of the sodium carboxymethylcellulose is at least about 100, preferably at least about 200. The sodium carboxymethylcellulose degree of polymerization can be up to about 4,000, preferably up to about 1,000. One exemplary suitable cellulose polymer is sodium carboxymethyl cellulose is sold under the tradename AQUALON 7L2P, 7 LF and 7LF PH, which is commercially available from Hercules Inc.

Advantageously, it has been found that particularly desirable compositions can be formed using HEC as the suspending agent and charged and/or salt form CMC (e.g., NaCMC) to ameliorate agglomeration of the 1H-indole-1-carboxamide. It has been further found that, when used in the same composition, HEC and NaCMC tend to exhibit a synergistic effect on viscosity. As such, preferred concentrations of HEC and NaCMC have been developed to address their use in the same composition, particularly when that composition is to be dispensed topically as drops to the eye. The concentration of HEC in the composition is at least about 0.05 w/v %, more typically at least about 0.1 w/v % and still more typically at least about 0.15 w/v %. Furthermore, the concentration of HEC in the composition is typically less than about 0.7 w/v %, more typically less than about 0.5 w/v % and still more typically less than about 0.3 w/v %. It is specifically contemplated that any of the lower limits on the concentration of HEC may be used in conjunction with any of the upper limits on the concentration of HEC. Preferred ranges for the concentration of HEC in the composition are as follows: at least about 0.05 w/v % but less than about 0.7 w/v %; at least about 0.1 w/v % but less than about 0.5 w/v %; at least about 0.15 w/v % but less than about 0.3 w/v %. When used, the concentration of NaCMC in the composition is at least about 0.3 w/v %, more typically at least about 0.6 w/v % and still more typically at least about 0.8 w/v % but is typically no greater than about 2.0 w/v %, more typically no greater than about 1.5 w/v % and still more typically no greater than about 1.3 w/v %. It is specifically contemplated that any of the lower limits on the concentration of NaCMC may be used in conjunction with any of the upper limits on the concentration of NaCMC. Preferred ranges for the concentration of NaCMC in the composition are as follows: at least about 0.3 w/v % but no greater than about 2.0 w/v %; at least about 0.6 w/v % but no greater than about 1.5 w/v %; at least about 0.8 w/v % but no greater than about 1.3 w/v %. Using a combination of HEC and NaCMC, at these concentrations, along with other ingredients discussed herein, will provide a desired viscosity to the composition that is at least 5 centipoise (cP), more at least about 12 cP and still more typically at least about 20 cP and is typically less than about 100 cP, more typically less than about 65 cP and still more typically less than about 50 cP. It is specifically contemplated that any of the lower limits on the concentration of HEC may be used in conjunction with any of the upper limits on the concentration of HEC. Preferred ranges for the viscosity of the composition, when it includes HEC and NaCMC, are as follows: at least about 5 cP but no greater than about 100 cP at least about 15 cP but no greater than about 65 cP; at least about 20 cP but no greater than about 50 cP.

When used, the combination of HEC and NaCMC, along with other ingredients discussed herein, in a suspension vehicle can provide significant advantage to the composition of the present invention. In particular, the composition can have a relatively long shelf life without any significant formation of agglomerated drug particles. Moreover, it has been found that relatively high concentrations of drug, such concentrations being disclosed herein, can be maintained in a suspended state without any significant agglomeration and can lower re-suspension times. This is particularly advantageous for the 1H-indole-1-carboxamide since these relatively high concentrations of 1H-indole-1-carboxamide have been found to be particularly efficacious when topically dosed to the eye and do not create any significant safety risks. Moreover, this ability is particularly surprising in view of the data provided herein suggesting that there may be multiple causes for agglomeration of the 1H-indole-1-carboxamide.

In one particularly preferred embodiment, the 1H-indole-1-carboxamide is relatively insoluble in water, but is yet still dissolved in the composition such that the composition is an aqueous solution and, preferably, an aqueous solution configured for topical multi-dose administration. Accordingly, it has been found that the 1H-indole-1-carboxamide can exhibit solubility in water of less than 0.01%, more typically less than 0.005%, even more typically less than 0.001% and even possibly less than 0.0008% at 25° C. and pH of 7 and yet still be dissolved at the concentrations of 1H-indole-1-carboxamide specified herein for the ophthalmic composition of the present invention. In this particular embodiment, it is typically desirable that the pH be relatively low. As used herein, the term dissolved or solubilized to form solution means that all of the 1H-indole-1-carboxamide is dissolved or solubilized in the composition or that only a nominal amount (i.e., less than 0.5 wt. % of the total weight) of the 1H-indole-1-carboxamide of the composition is not dissolved.

The concentration of 1H-indole-1-carboxamide, particularly N-(1-methyl-5-(trifluoromethyl)-1H-pyrazol-3-yl)-5-((6-((methylamino)methyl)pyrimidin-4-yl)oxy)-1H-indole-1-carboxamide, that can be dissolved in the composition of the present invention is typically greater than about 0.1 w/v %, more typically greater than about 0.4 w/v %, even more typically greater than about 1.0 w/v % and potentially greater than about 1.8 w/v % and even possibly greater than 2.5 w/v %. Moreover, the concentration of 1H-indole-1-carboxamide, particularly N-(1-methyl-5-(trifluoromethyl)-1H-pyrazol-3-yl)-5-((6-((methylamino)methyl)pyrimidin-4-yl)oxy)-1H-indole-1-carboxamide, that can be dissolved in the composition is typically less about 5.0 w/v %, more typically less than about 4.0 w/v % and even more typically less than about 3.3 w/v % and even possibly less than about 2.3 w/v %. It is specifically contemplated that any of the lower limits on the concentration of 1H-indole-1-carboxamide may be used in conjunction with any of the upper limits on the concentrations of 1H-indole-1-carboxamide. Preferred ranges for the concentration of 1H-indole-1-carboxamide, particularly N-(1-methyl-5-(trifluoromethyl)-1H-pyrazol-3-yl)-5-((6-((methylamino)methyl)pyrimidin-4-yl)oxy)-1H-indole-1-carboxamide, that can be dissolved in the composition are as follows: greater than about 0.4 w/v % but less than about 4.0 w/v %; greater than about 0.4 w/v % but less than about 3.3 w/v %; greater than about 1.8 w/v % but less than about 4.0 w/v %; and greater than about 1.8 w/v % but less than about 3.3 w/v %. The concentrations of 1H-indole-1-carboxamide herein refer to the concentration of the 1H-indole-1-carboxamide only and do not take into account the weight or concentration of the salt of the 1H-indole-1-carboxamide where the 1H-indole-1-carboxamide is provided in salt form within the composition.

It has been found that a special combination of excipients and or compositions conditions can dissolve the 1H-indole-1-carboxamide. In particular, dissolution of the 1H-indole-1-carboxamide can be achieved using a combination of one, two or more, and preferably all, of the following: cyclodextrin derivative, particularized pH adjustment agent, particularized pH.

The cyclodextrin derivative used to aid in solubilizing the 1H-indole-1-carboxamide is preferably β-cyclodextrin derivative, γ-cyclodextrin derivative or both. The specific amount of cyclodextrin derivative, particularly β-cyclodextrin derivative, γ-cyclodextrin derivative or combination thereof, in a particular composition will typically depend upon the type or combination of types of derivatives used. One particularly desirable β-cyclodextrin derivative is a hydroxy alkyl-β-cyclodextrin such as hydroxypropyl-β-cyclodextrin (HP-β-CD). Another particularly desirable γ-cyclodextrin derivative is a hydroxy alkyl-γ-cyclodextrin such as hydroxypropyl-γ-cyclodextrin (HP-γ-CD). Another particularly desirable β-cyclodextrin derivative is sulfoalkyl ether-β-cyclodextrin (SAE-β-CD), particularly sulfobutyl ether-β-cyclodextrin (SBE-β-CD). It is contemplated that a combination of hydroxypropyl-β-cyclodextrin, hydroxypropyl-γ-cyclodextrin and/or sulfoalkyl ether-β-cyclodextrin derivative may be employed in a single composition, but it is typically desirable to use only one of the three as the sole or substantially the sole (i.e., at least 90% by weight of the cyclodextrin component) cyclodextrin derivative. Hydroxypropy-β-cyclodextrin, hydroxypropyl-γ-cyclodextrin, either alone or in combination, are highly preferred cyclodextrin derivatives.

The cyclodextrin derivative, particularly the β-cyclodextrin derivative, γ-cyclodextrin derivative or combination thereof, and even more typically hydroxypropy-β-cyclodextrin, hydroxypropyl-γ-cyclodextrin or a combination thereof, is typically present in the composition at a concentration that is at least 1.5 w/v %, more typically at least 3.0 w/v %, even more possibly at least 3.5 w/v % and even possibly at least 4.5 w/v, but is typically no greater than 10.0 w/v %, more typically no greater than 7.2% w/v, even more typically no greater than 5.5 w/v % and even possibly no greater than 4.5 w/v. Preferably, the total concentration of cyclodextrin in the composition, particularly the β-cyclodextrin derivative, γ-cyclodextrin derivative or combination thereof, and even more typically hydroxypropy-β-cyclodextrin, hydroxypropyl-γ-cyclodextrin or a combination thereof, is at least 1.5 w/v % but no greater than 10.0 w/v %, more typically at least 3.5 w/v % but no greater than 7.2 w/v % and even more typically at least 4.5 w/v % but no greater than 5.5 w/v %.

Hydroxypropyl-γ-cyclodextrin is preferred for dissolution of the 1H-indole-1-carboxamide. Table I below shows that hydroxypropyl-γ-cyclodextrin is better than hydroxypropy-β-cyclodextrin in solubilizing the 1H-indole-1-carboxamide.

TABLE I

| Sample Description | 1H-indole-1-carboxamide* Solubility** (mg/mL) | pH |
|---|---|---|
| LHA510 in 1% HPβCD in Acetate | 7.50, 7.28 | 4.584 |
| LHA510 in 2.5% HPβCD in Acetate | 12.45, 12.45 | 4.606 |
| LHA510 in 5% HPβCD in Acetate | 19.61, 15.93 | 4.670 |
| LHA510 in 8% HPβCD in Acetate | 25.67, 25.67 | 4.530 |
| LHA510 in 10% HPβCD in Acetate | 30.59, 30.57 | 4.610 |
| LHA510 in 1% HPγCD in Acetate | 9.28, 9.09 | 4.607 |
| LHA510 in 2.5% HPγCD in Acetate | 14.73, 14.69 | 4.555 |
| LHA510 in 5% HPγCD in Acetate | 21.88, 22.34 | 4.505 |
| LHA510 in 8% HPγCD in Acetate | 30.66, 30.60 | 4.580 |
| LHA510 in 10% HPγCD in Acetate | 34.30, 34.56 | 4.668 |

*particularly,N-(1-methyl-5-(trifluoromethyl)-1H-pyrazol-3-yl)-5-((6-((methylamino)methyl)pyrimidin-4-yl)oxy)-1H-indole-1-carboxamide
**equilibrium solubility determined at day 3

It has been found that the cyclodextrin derivative, particularly the β-cyclodextrin derivative, γ-cyclodextrin derivative or combination thereof, and even more typically hydroxypropy-β-cyclodextrin, hydroxypropyl-γ-cyclodextrin or a combination thereof, tend to provide enhanced solubility of the 1H-indole-1-carboxamide when the composition additionally has a relatively low pH. Thus, depending upon the type of composition, the desired pH of the composition may be different. For compositions that include the cyclodextrin derivative, particularly the β-cyclodextrin derivative, γ-cyclodextrin derivative or combination thereof, and even more typically hydroxypropy-β-cyclodextrin, hydroxypropyl-γ-cyclodextrin or a combination thereof, the pH is preferably relatively low. The relatively low pH is typically at least 3.0, more typically at least 4.0 and even more typically at least 4.3, but is typically no greater than 5.5, more typically no greater than 5.0 and even more typically no greater than 4.7. It is also preferable that the pH of the composition be at least 4.0 but no greater than 5.0 and more preferably at least 4.3 but no greater than 4.7. Such compositions will typically be solutions in which the 1H-indole-1-carboxamide is dissolved. Table II below shows the enhanced solubility in relatively low pH in combination with the cyclodextrin derivative.

TABLE II

| Solubilizer/Buffer/pH | 1H-indole-1-carboxamide* Solubility (mg/mL) | Solubility Enhancement (fold)** | Final pH |
|---|---|---|---|
| 5% HP-β-CD/Acetate buffer/pH 4.5 | 11.67 | 1667 | 4.64 |
| 5% HP-β-CD/Phosphate buffer/pH 7 | 1.012 | 144 | 7.06 |

*particularly,N-(1-methyl-5-(trifluoromethyl)-1H-pyrazol-3-yl)-5-((6-((methylamino)methyl)pyrimidin-4-yl)oxy)-1H-indole-1-carboxamide
**compared to intrinsic solubility (approximately 0.007 mg/mL) at pH 7

It has also been found that the pH adjustment agent can have a significant effect on the solubility of the 1H-indole-1-carboxamide in the composition. Preferably, the pH adjustment agent is selected from the group consisting of sulfuric acid, phosphoric acid, lactic acid, acetic acid, glucoronic acid or methasulfonic acid and combinations thereof. The pH adjustment agent may also be selected from the group consisting of any subset of the aforementioned acids. One preferred subset is selected from the group consisting of sulfuric acid, phosphoric acid, acetic acid, lactic acid and combinations thereof since these acids are desirable for topical ophthalmic applications. Sulfuric acid is a particularly preferred pH adjustment agent since it is particularly desirable for topical ophthalmic application. Thus, in one embodiment, sulfuric acid is a substantial portion (at least 70 wt. %), substantially the entirety (at least 90 wt %) or the entirety of the pH adjustment agent.

Table III below shows the significant difference in solubility of the 1H-indole-1-carboxamide in compositions that have common pH adjustment agents such as hydrochloric acid and citric acid as compared to compositions that include the preferred acids of the composition of the present invention.

TABLE III

| Sample Information | pH Adjustment Agent** | 1H-indole-1-carboxamide* Solubility (mg/mL) | Final pH |
|---|---|---|---|
| 1H-indole-1-carboxamide* in 8% HP-γ-CD in acetate buffer | Hydrochloric acid | 15.47 | 4.887 |
| | Sulfuric acid | 35.58 | 4.973 |
| | Phosphoric acid | 25.44 | 5.014 |
| | Citric acid | 6.88 | 4.872 |
| | Lactic acid | 33.05 | 4.955 |
| | Acetic acid | 30.27 | 4.887 |
| | Glucoronic acid | 36.0 | 4.732 |
| | Methanesulfonic acid | 32.57 | 4.902 |

*particularly,N-(1-methyl-5-(trifluoromethyl)-1H-pyrazol-3-yl)-5-((6-((methylamino)methyl)pyrimidin-4-yl)oxy)-1H-indole-1-carboxamide
**all acids were 1N The amount of pH adjusting agent used to achieve the desired pH of the composition will vary depending upon the relative strength of the acid[s] being used to adjust the pH. For each of the preferred acids described herein, and particularly for acetic acid, the acid[s] will be added to the composition such that the acid[s] are in the composition at a concentration that is at least 0.001 w/v %, more typically at least 0.05 w/v % and even more typically at least 0.5 w/v %. The preferred acid[s], particularly acetic acid, will typically be added to the composition such that the acid[s] are in the composition at a concentration that is less than 2.0 w/v %. Of course, the skilled artisan will understand that pH adjustment can involve the use of both acid and base to achieve the desired pH. For example, when the pH is adjusted too low with acid, a base such as tromethamine, may be introduced to adjust the pH upward. It shall be further understood that, unless otherwise specifically stated, the acid[s] named herein as pH adjusting agents shall be considered to be pH adjusting agents for the purposes of a composition as long as they actually have the overall effect of lowering the pH of the composition and regardless of whether they are specifically provided to the composition at the time of adjusting pH. For example, acetic acid will be considered a pH adjusting agent of the composition of the present invention even if phosphoric acid is used, during processing, to adjust the pH of the composition as long as the acetic acid is present in the composition and has the overall effect of lowering the pH of the composition.

As suggested above, the 1H-indole-1-carboxamide dosed topically to the eye with the composition of the present invention can advantageously provide relatively high concentrations of 1H-indole-1-carboxamide at the back of the eye, particularly the retina, for treating ocular condition or disease such as AMD. In a preferred embodiment, the composition of the present invention, after dosing and measurement in rabbits according to example 2 below, provides a mean $AUC_{(0-last)}$ that is at least 4000 ng*h/g, more typically at least 6000 ng*h/g and even possibly at least 8000 ng*h/g at the retina. Also in a preferred embodiment, the composition of the present invention, after dosing and measurement according to example 2 below, provides a mean $AUC_{(0-last)}$ that is at least 300,000 ng*h/g, more typically at least 400,000 ng*h/g and even possibly at least 450,000 ng*h/g at the choroid.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples to be considered as exemplary only with a true scope and spirit of the invention being indicated by the following claims and equivalents thereof.

Table A below provides a listing of exemplary ingredients suitable for an exemplary preferred formulation of the ophthalmic composition (i.e., aqueous is suspension) of the present invention and desired weight/volume percentages for those ingredients.

TABLE A

| Ingredient | w/v percent |
| --- | --- |
| 1H-indole-1-carboxamide | 0.5 or 1.0 or 2.0 or 3.0 |
| Tyloxapol | 0.05 |
| Hydroxyethyl Cellulose (Natrosol 250HR) | 0.4 |
| Sodium Chloride | 0.4 |
| Boric Acid | 0.3 |
| Mannitol | 0.3 |
| Propylene Glycol | 0.55 |
| Benzalkonium chloride | 0.01 |
| Sodium Hydroxide/Hydrochloric Acid | sufficient to achieve approximately pH = 7.4 |
| Purified Water | Q.S. 100 |

It is understood that the weight/volume percents in table A can be varied by ±10%, ±20%, ±30%, ±90% of those weight/volume percents or more and that those variances can be specifically used to create ranges for the ingredients of the present invention. For example, an ingredient weight/volume percent of 10% with a variance of ±20% means that the ingredient can have a weight/volume percentage range of 8 to 12 w/v %.

Table AA below provides a listing of exemplary ingredients suitable for another exemplary preferred formulation of the ophthalmic composition (i.e., aqueous suspension) of the present invention and desired weight/volume percentages for those ingredients.

TABLE AA

| Ingredient | w/v percent |
| --- | --- |
| 1H-indole-1-carboxamide | 0.5 or 1.0 or 2.0 or 3.0 |
| Tyloxapol | 0.05 |
| Hydroxyethyl Cellulose (Natrosol 250HR) | 0.2 |
| NaCMC | 1.0 |
| Sodium Chloride | 0.4 |
| Boric Acid | 0.3 |
| Mannitol | 0.3 |
| Propylene Glycol | 0.55 |
| Benzalkonium chloride | 0.01 |
| Sodium Hydroxide/Hydrochloric Acid | sufficient to achieve approximately pH = 7.4 |
| Purified Water | Q.S. 100 |

It is understood that the weight/volume percents in table AA can be varied by ±10%, ±20%, ±30%, ±90% of those weight/volume percents or more and that those variances can be specifically used to create ranges for the ingredients of the present invention. For example, an ingredient weight/volume percent of 10% with a variance of ±20% means that the ingredient can have a weight/volume percentage range of 8 to 12 w/v %.

Table AAA below provides a listing of exemplary ingredients suitable for an exemplary preferred formulation of the ophthalmic composition (i.e., aqueous solution) of the present invention and desired weight/volume percentages for those ingredients.

TABLE AAA

| Ingredient | w/v percent |
| --- | --- |
| 1H-indole-1-carboxamide | 2.0 |
| Hydroxypropy-β-cyclodextrin, Hydroxypropyl-γ-cyclodextrin or a combination | 5 |
| Acetic Acid | 0.06 |
| Boric Acid | 0.3 |
| Mannitol, Propylene Glycol, Glycerin or a combination thereof | 1.5 |
| Propylene Glycol | 0.55 |
| Glycerin | 0.35 |
| Polymeric Quaternary Ammonium Compound | 0.001 |
| Sulfuric Acid/Tromethamine | sufficient to achieve approximately pH = 4.5 |
| Purified Water | Q.S. 100 |

It is understood that the weight/volume percents in table AAAA can be varied by ±10%, ±20%, ±30%, ±90% of those weight/volume percents or more and that those variances can be specifically used to create ranges for the ingredients of the present invention. For example, an ingredient weight/volume percent of 10% with a variance of ±20% means that the ingredient can have a weight/volume percentage to range of 8 to 12 w/v %.

The following examples are presented to further illustrate selected embodiments of the present invention. The formulations shown in the examples were prepared using procedures that are well-known to persons of ordinary skill in the field of ophthalmic pharmaceutical compositions.

EXAMPLES

Example 1

Table AB below provides five ophthalmic vehicles. Each of the vehicles were formulated into ophthalmic compositions that include 1.0 w/v % 1H-indole-1-carboxamide. The primary in vivo model to study efficacy of the 1H-indole-1-carboxamide was the Brown Norway rat laser-induced choroidal neovascularization (CNV) model. CNV area is measured 11 days after laser application by administering a vascular label i.v., fixing the eyes, and mounting the isolated posterior eye cup onto a microscope slide. The CNV on each flat mount is then imaged by fluorescent microscopy. The CNV area is measured with semi-automated software with analysis and exclusions completed on masked data. Rats have 4 laser burns applied to both eyes. Each group has n=8, 10 or 12 rats yielding 64, 80 or 96 data points per group, respectively.

TABLE AB

Formulations tested

| Formulation | Suspension/Solution |
|---|---|
| Solution A | 1N HCL, Cremophor ELP, PEG 400, 2M Tris in water |
| Solution B | Povidone K29/32, Tyloxapol, acetic acid, boric acid, Mannitol, propylene glycol, polyquaterium-1 |
| Suspension A | Mannitol, sodium chloride, propylene glycol, boric acid, carbopol 974P, Tyloxapol, benzalkonium chloride in purified water. |
| Suspension B | Ethanol, PEG 400, Pluronic F68 in phosphate buffer |
| Suspension C | Tyloxapol, Hydroxyethyl Cellulose (Natrosol 250HR), Sodium Chloride, Boric Acid, Mannitol, Propylene Glycol, Benzalkonium chloride, Sodium Hydroxide/Hydrochloric Acid, Purified Water |

Figure 2:
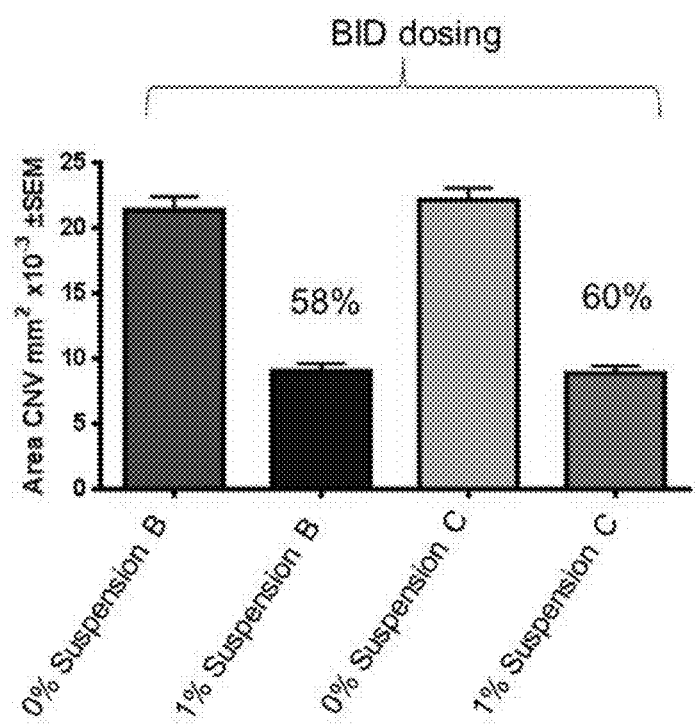
FIG. 2. is a graph illustrating the efficacy of an additional multi-dose topical ophthalmic compositions containing a 1H-indole-1-carboxamide as compared to a control containing 0% 1H-indole-1-carboxamide.

The ophthalmic compositions and vehicle were topically dosed at a volume of 4 µl per eye to both eyes. As can be seen in FIG. 1 and FIG. 2, a similar level of potency and efficacy has been observed for the compositions. No significant difference is observed between equivalent dosing frequency and concentrations. All groups dosed with the ophthalmic compositions significantly inhibit CNV compared to vehicle (p<0.001). All values are mean choroidal neovascularization area ±SEM. Percentage inhibition of laser-induced CNV is calculated by ratio of area in CNV in rats treated with 1H-indole-1-carboxamide compared to area in vehicle treated rats. CNV area to was analyzed by an ANOVA with a Neuman-keuls post hoc analysis. No significant difference was observed between composition dosed b.i.d. or between compositions dosed t.i.d. All 1% formulations significantly inhibited laser CNV compared to vehicle (p<0.001).

Example 2

A single unilateral dose (30 µL) of a preferred ophthalmic suspension composition (i.e., suspension C-2 in Example 3 below) of the present invention was dosed onto the right (OD) eye of pigmented NZW×NZR rabbits at 0.5%, 1%, and 2% N-(1-methyl-5-(trifluoromethyl)-1H-pyrazol-3-yl)-5-((6-((methylamino)methyl)pyrimidin-4-yl)oxy)-1H-indole-1-carboxamide. The N-(1-methyl-5-(trifluoromethyl)-1H-pyrazol-3-yl)-5-((6-((methylamino)methyl)pyrimidin-4-yl)oxy)-1H-indole-1-carboxamide was rapidly absorbed ($T_{max}$=0.5-3 hours) in all of the ocular tissues and plasma, except for RPE/choroid for which the $T_{max}$ ranged between 18 and 48 hours. N-(1-methyl-5-(trifluoromethyl)-1H-pyrazol-3-yl)-5-((6-((methylamino)methyl)pyrimidin-4-yl)oxy)-1H-indole-1-carboxamide $C_{max}$ and $AUC_{last}$ values, from highest to lowest, were observed in cornea, RPE/choroid and retina.

Figure 3:
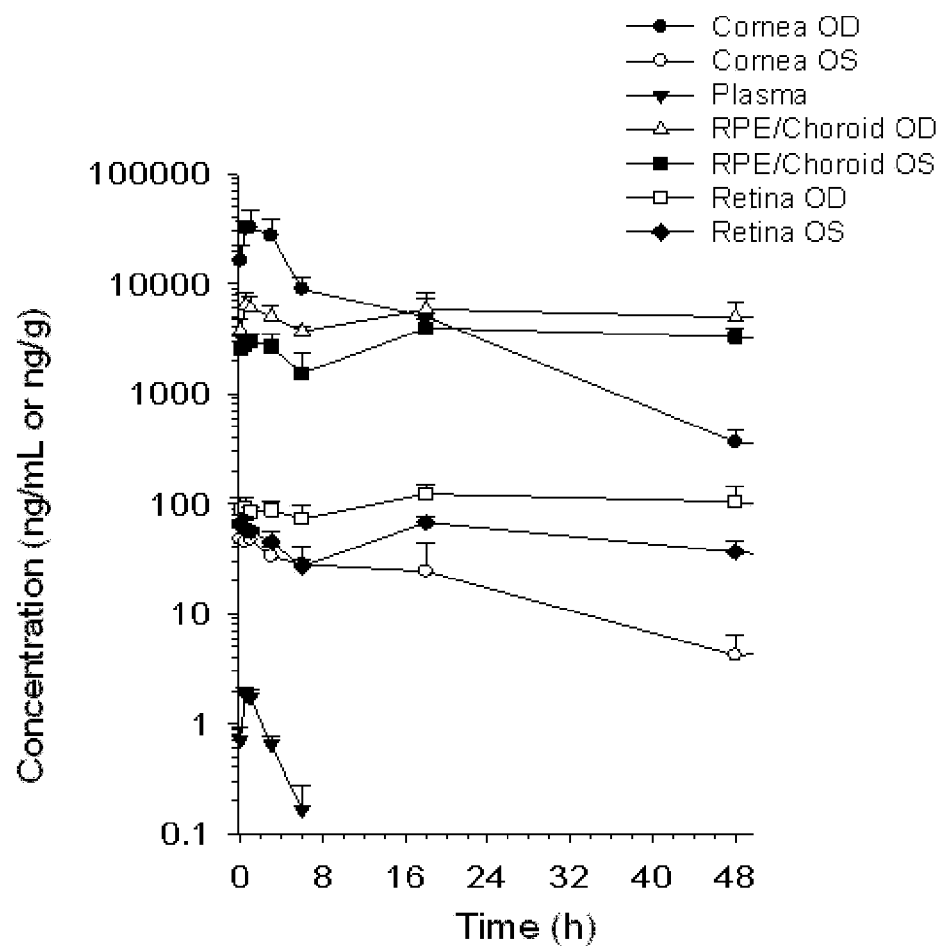
FIG. 3 is a graph of concentration N-(1-methyl-5-(trifluoromethyl)-1H-pyrazol-3-yl)-5-((6-((methylamino) methyl)pyrimidin-4-yl)oxy)-1H-indole-1-carboxamide versus time at multiple locations of the eye after dosing of a topical aqueous ophthalmic composition containing the N-(1-methyl-5-(trifluoromethyl)-1H-pyrazol-3-yl)-5-((6-((methylamino)methyl)pyrimidin-4-yl)oxy)-1H-indole-1-carboxamide.

Following monocular administration of 2% N-(1-methyl-5-(trifluoromethyl)-1H-pyrazol-3-yl)-5 #6-((methylamino)methyl)pyrimidin-4-yl)oxy)-1H-indole-1-carboxamide t.i.d. for 7 days to pigmented rabbits, systemic N-(1-methyl-5-(trifluoromethyl)-1H-pyrazol-3-yl)-5-((6-((methylamino)methyl)pyrimidin-4-yl)oxy)-1H-indole-1-carboxamide exposure was low with the mean $C_{max}$ of 1.85 ng/mL and $AUC_{last}$ of 5.12 ng*h/mL. There was no evidence of plasma accumulation as also illustrated in FIG. 3. As shown in Table C below, N-(1-methyl-5-(trifluoromethyl)-1H-pyrazol-3-yl)-5-((6-((methylamino)methyl)pyrimidin-4-yl)oxy)-1H-indole-1-carboxamide was present in the cornea, RPE/choroid and retina, with mean $AUC_{last}$ of 317000 ng*h/g in cornea, 453000 ng*h/g in RPE/choroid and 8400 ng*h/g in retina. In the contralateral undosed eyes of the 2% t.i.d treatment group, N-(1-methyl-5-(trifluoromethyl)-1H-pyrazol-3-yl)-5-((6-((methylamino)methyl)pyrimidin-4-yl)oxy)-1H-indole-1-carboxamide exposure was lower with the $AUC_{last}$ values of 1260 ng*h/g in cornea, 293000 ng*h/g in RPE/choroid and 3640 ng*h/g in retina. The higher N-(1-methyl-5-(trifluoromethyl)-1H-pyrazol-3-yl)-5-((6-((methylamino)methyl)pyrimidin-4-yl)oxy)-1H-indole-1-carboxamide exposure in the dosed eyes indicates local penetration to the target tissues in the dosed eyes, which accounted for 37.1% and 56.7% of the total $AUC_{last}$ in RPE/choroid and retina, respectively.

PK parameters of 1H-indole-1-carboxamide in ocular tissues and plasma following repeated t.i.d. monocular OD dosing for 7 days of 2% N-(1-methyl-5-(trifluoromethyl)-1H-pyrazol-3-yl)-5-((6-((methylamino)methyl)pyrimidin-4-yl)oxy)-1H-indole-1-carboxamide formulation in pigmented rabbits employing suspension C-2 in Table B below.

TABLE B 1H-indole-1-carboxamide

| Matrix | $T_{max}$ (h) | $C_{max}$ (ng/mL or ng/g) | | $AUC_{last}$ (ng*h/mL or ng*h/g) | |
|---|---|---|---|---|---|
| | | Mean | SD | Mean | SD |
| Cornea OD | 1 | 32300 | 14000 | 317000 | 30900 |
| Cornea OS | 0 | 47.5 | 15.5 | 1260 | 227 |
| RPE/Choroid OD | 0.5 | 6410 | 1840 | 453000 | 46900 |
| RPE/Choroid OS | 18 | 3950 | 850 | 293000 | 17000 |
| Retina OD | 18 | 122 | 29.3 | 8400 | 828 |
| Retina OS | 18 | 67.2 | 9.95 | 3640 | 238 |
| Plasma | 0.5 | 1.85 | 0.305 | 5.12 | 0.283 |

OD: Right Eye (Dosed); OS: Left Eye (Undosed); SD: Standard Deviation
Plasma in units of ng/mL and ng*h/mL for $C_{max}$ and $AUC_{last}$; The ocular tissues in units of ng/g and ng*h/g for $C_{max}$ and $AUC_{last}$; $T_{last}$ = 96 h Four suspensions using HEC/tyloxapol and Carbopol/polysorbate 80 vehicles as were developed to evaluate efficacy in rat CNV model. The suspensions are presented below in Table C.

TABLE C

Suspensions of N-(1-methyl-5-(trifluoromethyl)-1H-pyrazol-3-yl)-5-((6-((methylamino)methyl)pyrimidin-4-yl)oxy)-1H-indole-1-carboxamide

| | Formulation Examples | | | |
|---|---|---|---|---|
| Component | Sup A-1 | Susp A-2 | Susp C-1 | Susp C-2 |
| | Amount (% w/v) | | | |
| 1H-indole-1-carboxamide | 1.0 | 3.0 | 1.0 | 3.0 |
| Carbopol 974p | 0.45 | 0.45 | — | — |
| Hydroxyethyl cellulose 250HR | — | — | 0.4 | 0.4 |
| Sodium Chloride | 0.45 | 0.45 | 0.4 | 0.40 |
| Tyloxapol | — | — | 0.05 | 0.05 |
| Polysorbate 80 | 0.05 | 0.05 | — | — |

TABLE C-continued

Suspensions of N-(1-methyl-5-(trifluoromethyl)-1H-pyrazol-3-yl)-
5-((6-((methylamino)methyl)pyrimidin-4-yl)oxy)-1H-indole-
1-carboxamide

| | Formulation Examples | | | |
|---|---|---|---|---|
| Component | Sup A-1 | Susp A-2 | Susp C-1 | Susp C-2 |
| | Amount (% w/v) | | | |
| Boric acid | — | — | 0.3 | 0.3 |
| Mannitol | 2.0 | 2.0 | 0.3 | 0.3 |
| Propylene glycol | — | — | 0.55 | 0.55 |
| Benzalkonium chloride | 0.01 | 0.01 | 0.01 | 0.01 |
| Sodium hydroxide | Q.s. to pH 7.4 | Q.s. to pH 7.4 | Q.s. to pH 7.4 | Q.s. to pH 7.4 |
| Hydrochloric acid | Q.s. to pH 7.4 | Q.s. to pH 7.4 | Q.s. to pH 7.4 | Q.s. to pH 7.4 |
| Purified water | Q.s. to 100 | Q.s. to 100 | Q.s. to 100 | Q.s. to 100 |

The data from the rat CNV study suggests that 3% N-(1-methyl-5-(trifluoromethyl)-1H-pyrazol-3-yl)-5-((6-((methylamino)methyl)pyrimidin-4-yl)oxy)-1H-indole-1-carboxamide suspension in both HEC (Susp C-2) and Carbopol (Susp A-2) based formulations dosed QD are effective, however the Carbopol based formulation (Susp A-2) leads to a reduction in efficacy. A similar result was observed employing a 1% N-(1-methyl-5-(trifluoromethyl)-1H-pyrazol-3-yl)-5-((6-((methylamino)methyl)pyrimidin-4-yl)oxy)-1H-indole-1-carboxamide suspension in Carbopol formulation (Susp A-1) dosed BID which exhibited significantly reduced efficacy (about 30% inhibition of choroidal neovascularization with Carbopol based formulation) compared to the HEC containing formulation, Sup C-1 (Table D below).

TABLE D

Efficacy Results of N-(1-methyl-5-(trifluoromethyl)-1H-pyrazol-3-yl)-
5-((6-((methylamino)methyl)pyrimidin-4-yl)oxy)-1H-indole-1-
carboxamide Suspensions

| | Veh C-1 & C-2 | Susp C-1 | Susp C-2 | Veh A-1 & A-2 | Susp A-1 | Susp A-2 |
|---|---|---|---|---|---|---|
| Number of values | 87 | 91 | 93 | 86 | 87 | 94 |
| Dose regimen | BID | BID | QD | BID | BID | QD |
| Mean | 22.13 | 8.874 | 7.199 | 21.03 | 14.95 | 9.921 |
| Std. Deviation | 8.641 | 5.374 | 4.219 | 7.606 | 8.598 | 4.34 |
| Std. Error | 0.9264 | 0.5634 | 0.4375 | 0.8202 | 0.9218 | 0.4476 |
| % Inhibition | 0.0% | 59.9% | 67.5% | 0.0% | 28.9% | 52.8% |

A settling study was conduct for suspension compositions that included HEC only, NaCMC only and the combination of HEC and NaCMC. The results are to provided in Table E below.

TABLE E

| | 2% LHA510 Suspension Formulation # | | | | | |
|---|---|---|---|---|---|---|
| Description | 1 | 2 | 3 | 4 | 5 | 6 |
| | Amount (% w/v) | | | | | |
| LHA510 | 2.0 | 2.0 | 2.0 | 2.0 | 2.0 | 2.0 |
| Tyloxapol | 0.05 | 0.05 | 0.05 | 0.05 | 0.05 | 0.05 |

TABLE E-continued

| | 2% LHA510 Suspension Formulation # | | | | | |
|---|---|---|---|---|---|---|
| Description | 1 | 2 | 3 | 4 | 5 | 6 |
| | Amount (% w/v) | | | | | |
| Hydroxyethyl Cellulose (Natrosol 250HR) | 0.4 | 0.4 | 0.15 | 0.15 | 0.15 | — |
| Sodium CMC 7LFPH | — | 0.1 | 1.0 | 1.0 | 1.0 | 1.0 |
| Sodium Chloride | 0.4 | — | 0.4 | — | — | 0.4 |
| Boric Acid | 0.3 | 0.3 | 0.3 | 0.3 | 0.3 | 0.3 |
| Mannitol | 0.3 | 0.3 | 0.3 | 0.3 | 0.3 | 0.3 |
| Propylene Glycol | 0.55 | 1.5 | 0.55 | 1.5 | 0.55 | 0.55 |
| Glycerin | — | — | — | — | 1.2 | — |
| Benzalkonium chloride | 0.01 | 0.01 | 0.01 | 0.01 | 0.01 | 0.01 |
| Sodium Hydroxide | Adjust pH to 7.4 | | | | | |
| Hydrochloric Acid | Adjust pH to 7.4 | | | | | |
| Purified Water | q.s to 100 | | | | | |

Formulations 3, 4, 5 and 6, as opposed to formulations 1 and 2, were all flocculated, non-caking systems that, after settling, were easily redispersible upon shaking of the compositions. Such study indicates that use of NaCMC, particularly at certain concentrations, can aid in forming a highly desirable, redispersible, flocculated suspension of the 1H-indole-1-carboxamide.

The ability of NaCMC to aid in forming these desirable suspensions systems was surprisingly discovered after failure of a variety of other additives to create a flocculated, non-caking and easily redispersible system. It was determined that NaCMC unexpectedly provide the 1H-indole-1-carboxamide with desired Zeta Potential. In particular, NaCMC creates repulsive forces between the particles of 1H-indole-1-carboxamide. Table F below shows the difference in Zeta Potential provided by the NaCMC as compared to a sampling of other excipients that were tried. Notably, the other excipients are from a variety of other potential genus of excipients including salts, surfactants, polymer and polymeric acids.

TABLE F

| Additive[a] | Zeta Potential (mV) |
|---|---|
| None | −2.58 |
| 10 mM NaCl | 0.6 |
| 0.1% Pluronic F127 | −1.09 |
| 1% Pluronic F127 | −0.962 |
| 0.5% Sodium CMC 7LF PH | −40.3 |
| 1% Sodium CMC 7LF PH | −47.8 |
| 1% Vitamin E TPGS | −1.77 |
| 1% Povidone (PVP 29/32)[b] | 0 |
| 1% Polyvinyl phosphoric acid (PVPA) | −0.835 |

[a]dispersant was deionized water
[b]zeta potential could not be measured since PVP dissolved LHA510 particles It was also surprisingly discovered that BAK was a highly superior preservative efficacy for formulations containing both NaCMC and HEC. In particular, a relatively low concentration of BAK showed highly superior preservative efficacy relative to polyquaternium-1, which is considered to be a normally highly effective preservative. The results of such comparison are provided below in Table G.

TABLE G

| Formulation Component | AAA | BBB |
|---|---|---|
| | Amount (w/v %) | |
| Hydroxyethyl cellulose (Natrosol 250HR) | 0.2 | 0.2 |
| Sodium Carboxymethylcellulose 7LFPH | 1.0 | 1.0 |
| Sodium Chloride | 0.4 | 0.4 |
| Tyloxapol | 0.05 | 0.05 |
| Boric Acid | 0.3 | 0.3 |
| Mannitol | 0.3 | 0.3 |
| Propylene Glycol | 0.55 | 0.55 |
| Benzalkonium Chloride | 0.005 | — |
| Polyquaternium-1 | — | 0.001 |
| Sodium Hydroxide | Qs to pH 7.4 | Qs to pH 7.4 |
| Hydrochloric Acid | Qs to pH 7.4 | Qs to pH 7.4 |
| Purified Water | Qs to 100% | Qs to 100% |
| PET | Log$_{10}$ Unit Reduction | |
| S. aureus 6 h/24 h/7 d/14 d/28 d | 5.0/5.0/5.0/5.0/5.0 | 0.0/0.1/2.4/5.0/NT$^a$ |
| P. aerugin 6 h/24 h/7 d/14 d/28 d | 5.0/5.0/5.0/5.0/5.0 | 0.0/0.2/0.0/0.0/NT |
| E. coli 6 h/24 h/7 d/14 d/28 d | 5.1/5.1/5.1/5.1/5.1 | 0.0/0.0/0.0/0.0/NT |
| C. albican 7 d/14 d/28 d | 5.0/5.0/5.0 | 0.2/0.3/NT |
| A. Brasiliensis 7 d/14 d/28 d | 5.0/5.0/5.0 | 2.8/2.1/NT |

$^a$NT: Not tested

Three highly preferred topical aqueous compositions having 1H-indole-1-carboxamide dissolved therein to form a topical aqueous multi-dose solution are provided in Table H below.

TABLE H

| Formulation Component | AA | BB | CC |
|---|---|---|---|
| | Amount (% w/v) | | |
| 1H-indole-1-carboxamide* | 2 | 2 | 2 |
| Hydroxypropyl-γ-Cyclodextrin | 5 | 4 | 4 |
| PVP C30 | — | 4 | — |
| Tyloxapol | — | — | 0.25 |
| Acetic Acid | 0.06 | 0.06 | 0.06 |
| Boric Acid | 0.3 | 0.3 | 0.3 |
| Mannitol | 0.3 | 0.3 | 0.3 |
| Propylene Glycol | 0.8 | 0.8 | 0.8 |
| Glycerin | 0.35 | 0.35 | 0.35 |
| Polyquaternium-1 | 0.001 | 0.001 | 0.001 |
| Sulfuric Acid/Tromethamine | Qs to pH 4.5 | Qs to pH 4.5 | Qs to pH 4.5 |
| Purified Water | Qs to 100% | Qs to 100% | Qs to 100% |

*N-(1-methyl-5-(trifluoromethyl)-1H-pyrazol-3-yl)-5-((6-((methylamino)methyl)pyrimidin-4-yl)oxy)-1H-indole-1-carboxamide Each of the compositions of Table H showed desirable stability and the 1H-indole-1-carboxamide substantially remained in solution over extended time periods and/or at elevated temperature conditions. The results of stability testing for the three compositions are provided below in Table I. The compositions of Table I were disposed in 4 mL opaque LDPE containers.

TABLE I

| | | 1H-indole-1-carboxamide* Assay (as % of Initial)** | | |
|---|---|---|---|---|
| Time | | Composition Identifier | | |
| Condition | (wks) | AA | BB | CC |
| 40° C. | 4 | 98.3 | 97.6 | 98.0 |
| 40° C. | 8 | 97.3 | 94.4 | 94.9 |
| 40° C. | 13 | 95.6 | NT | NT |

TABLE I-continued

| | | 1H-indole-1-carboxamide* Assay (as % of Initial)** | | |
|---|---|---|---|---|
| Time | | Composition Identifier | | |
| Condition | (wks) | AA | BB | CC |
| 40° C. | 26 | 90.5 | NT | NT |
| 5° C. | 4 | 100.5 | 101.1 | 99.7 |

*N-(1-methyl-5-(trifluoromethyl)-1H-pyrazol-3-yl)-5-((6-((methylamino)methyl)pyrimidin-4-yl)oxy)-1H-indole-1-carboxamide
**study ongoing
NT: Not Tested This data shows that compositions AA, BB and CC, but particularly composition AA, is likely to exhibit desired stability for 18 months or longer when stored in an opaque container at 2-8° C.

Table J below illustrates preservation efficacy testing for composition AA. As can be seen, composition AA can pass even the stringent preservation efficacy standards of EP A referenced above.

TABLE J

| | Log$_{10}$ Unit Reduction | | | | |
|---|---|---|---|---|---|
| Organisms | 6 hour | 24 hour | day 7 | day 14 | day 28 |
| S. aureus | 3.9$^a$ | 3.9 | 3.9 | 3.9 | 3.9 |
| P. aeruginosa | 3.9$^a$ | 3.9 | 3.9 | 3.9 | 3.9 |
| E. coli | 5.0 | 5.0 | 5.0 | 5.0 | 5.0 |
| C. albicans | N/A | N/A | 4.9 | 4.9 | 4.9 |
| A. brasiliensis | N/A | N/A | 2.9 | 3.0 | 2.2 |

$^a$variability was due to limit of detection

What is claimed is:

1. A multi-dose aqueous suspension ophthalmic composition, comprising:
a 1H-indole-1-carboxamide of formula I below:

or a pharmaceutically acceptable salt thereof, wherein:
$R_1$ is hydrogen or $C_1$-$C_6$alkyl;
$R_3$ is hydrogen or $C_1$-$C_6$alkyl;
$R_5$ is hydrogen or halogen;
$R_7$ is hydrogen or $C_1$-$C_6$alkyl;
X is O or S;
$R_8$ is selected from the group consisting of hydrogen and $C_1$-$C_4$alkyl;
$R_9$ is selected from the group consisting of $(CR_{11}R_{12})_n$$NR_{13}R_{14}$, $(CR_{11}R_{12})_n$heterocycle, $(CR_{11}R_{12})_n$$OR_{15}$, $(CR_{11}R_{12})_n$$C(O)ER_{13}$, and $(CR_{11}R_{12})_n$$S(O)_m$$R_{17}$; or
$R_8$ and $R_9$, taken in combination together with the atoms to which they are attached form a saturated 4-7 membered heterocyclic ring having 1 or 2 ring heteroatoms selected from N, O or S, which heterocyclic ring is substituted with 0, 1, or 2 groups independently selected from the group consisting of $C_1$-$C_6$alkyl, $C_1$-$C_6$haloalkyl, halogen, hydroxy$C_1$-$C_6$alkyl, amino$C_1$-$C_6$alkyl, $C_3$-$C_7$cycloalkyl$C_1$-$C_4$alkyl, heterocycle$C_1$-$C_4$alkyl, $C_1$-$C_6$alkanoyl, mono- and di-$C_1$-$C_6$alkylaminocarbonyl, $C_1$-$C_6$alkoxycarbonyl, and $C_1$-$C_6$alkylsulfonyl;

$Ar_2$ is phenyl, naphthyl, 5 or 6 membered monocyclic heteroaryl, wherein each heteroaryl has 1, 2, or 3 ring heteroatoms selected from N, O or S and wherein the phenyl, naphthyl, or heteroaryl group is unsubstituted or substituted by 1, 2, or 3 groups independently selected from the group consisting of $C_1$-$C_6$alkyl, $C_1$-$C_6$haloalkyl, halo, hydroxyl, $CO_2C_1$-$C_6$alkyl, phenyl, and $C_3$-$C_7$cycloalkyl;

m is 0, 1, or 2;

n is 1, 2, or 3;

E is O or $NR_{18}$;

$R_{11}$, $R_{12}$ and $R_{18}$ are the same or different and are independently selected at each occurrence from the group consisting of hydrogen and $C_1$-$C_4$alkyl; and $R_{13}$, $R_{14}$, $R_{15}$, $R_{16}$ and $R_{17}$ are independently selected at each occurrence from the group consisting of hydrogen, $C_1$-$C_6$alkyl, $C_3$-$C_6$cycloalkyl, phenyl and heterocycle, each of which is substituted with 0, 1 or 2 groups independently selected from hydroxyl, amino, and mono- and di-$C_1$-$C_6$alkylamino; and wherein the concentration of 1H-indole-1-carboxamide in the composition is greater than 1.0 w/v % but less than 4.0 w/v %;

an ophthalmic vehicle comprised at least 80 w/v % water, a suspending agent that suspends the 1H-indole-1-carboxamide, a charged and/or salt form of carboxymethylcellulose (CMC), a preservative, and an ingredient selected from the group consisting of a surfactant, a buffer, a polyol, and an osmolality agent;

wherein the preservative is benzalkonium chloride;

wherein the composition has a pH in the range of 6.4 to 7.6 and an osmolality of 200 to 450 mOsm/kg and wherein the suspending agent is hydroxyethylcellulose (HEC).

2. An ophthalmic composition as in claim 1 wherein the composition includes the buffer and the polyol and wherein the buffer is borate.

3. An ophthalmic composition as in claim 2 wherein the polyol is selected from the group consisting of mannitol, sorbitol, propylene glycol, glycerol and combinations thereof.

4. An ophthalmic composition as in claim 3 wherein the mannitol and/or sorbitol is in the composition at a concentration that is greater than 0.15 w/v % but less than 0.5 w/v %, the propylene glycol and/or glycerol is in the composition at a concentration that is greater than 0.5 w/v % but less than 1.8 w/v % and the borate is in the composition at a concentration that is greater than 0.1 w/v % but less than 0.4 w/v %.

5. An ophthalmic composition as in claim 1 wherein the 1H-indole-1-carboxamide is selected from the group consisting of:

N-(4-fluoro-3-(trifluoromethyl)phenyl)-5-(6-((methylamino)methyl)pyrimidin-4-yloxy)-1H-indole-1-carboxamide;

5-(6-(hydroxymethyl)pyrimidin-4-yloxy)-N-(3-(trifluoromethyl)phenyl)-1H-indole-1-carboxamide;

5-(6-(methoxymethyl)pyrimidin-4-yloxy)-N-(3-(trifluoromethyl)phenyl)-1H-indole-1-carboxamide;

5-(6-((methylamino)methyl)pyrimidin-4-yloxy)-N-(3-(trifluoromethyl)phenyl)-1H-indole-1-carboxamide;

5-(6-((dimethylamino)methyl)pyrimidin-4-yloxy)-N-(3-(trifluoromethyl)phenyl)-1H-indole-1-carboxamide;

5-(2-((methylamino)methyl)pyridin-4-yloxy)-N-(3-(trifluoromethyl)phenyl)-1H-indole-1-carboxamide;

5-(6-((2H-tetrazol-2-yl)methyl)pyrimidin-4-yloxy)-N-(4-fluoro-3-(trifluoromethyl)phenyl)-1H-indole-1-carboxamide;

5-(6-((cyclopropylamino)methyl)pyrimidin-4-yloxy)-N-(4-fluoro-3-(trifluoromethyl)phenyl)-1H-indole-1-carboxamide;

N-(2-fluoro-3-(trifluoromethyl)phenyl)-5-(6-((methylamino)methyl)pyrimidin-4-yloxy)-1H-indole-1-carboxamide;

5-(6-((cyclopropylamino)methyl)pyrimidin-4-yloxy)-N-(2-fluoro-3-(trifluoromethyl)phenyl)-1H-indole-1-carboxamide;

N-(4-fluoro-3-(trifluoromethyl)phenyl)-5-(6-(methylsulfonylmethyl)pyrimidin-4-yloxy)-1H-indole-1-carboxamide;

5-(7-ethyl-5,6,7,8-tetrahydropyrido[3,4-d]pyrimidin-4-yloxy)-N-(4-fluoro-3-(trifluoromethyl)phenyl)-1H-indole-1-carboxamide;

5-(7-propyl-5,6,7,8-tetrahydropyrido[3,4-d]pyrimidin-4-yloxy)-N-(3-(trifluoromethyl)phenyl)-1H-indole-1-carboxamide;

5-(7-isopropyl-5,6,7,8-tetrahydropyrido[3,4-d]pyrimidin-4-yloxy)-N-(3-(trifluoromethyl)phenyl)-1H-indole-1-carboxamide;

5-(7-methyl-5,6,7,8-tetrahydropyrido[3,4-d]pyrimidin-4-yloxy)-N-(3-(trifluoromethyl)phenyl)-1H-indole-1-carboxamide;

5-(6,7-dihydro-5H-pyrrolo[3,4-d]pyrimidin-4-yloxy)-N-(3-(trifluoromethyl)phenyl)-1H-indole-1-carboxamide;

4-fluoro-5-(5,6,7,8-tetrahydropyrido[3,4-d]pyrimidin-4-yloxy)-N-(3-(trifluoromethyl)phenyl)-1H-indole-1-carboxamide;

5-(6-((methyl amino)methyl)pyrimidin-4-yloxy)-N-(3-(trifluoromethyl)-1H-pyrazol-5-yl)-1H-indole-1-carboxamide;

N-(2-fluoro-5-(trifluoromethyl)phenyl)-5-(5,6,7,8-tetrahydropyrido[3,4-d]pyrimidin-4-yloxy)-1H-indole-1-carboxamide;

4-fluoro-5-(6-((methylamino)methyl)pyrimidin-4-yloxy)-N-(5-(trifluoromethyl)-1H-pyrazol-3-yl)-1H-indole-1-carboxamide;

N-(5-tert-butylisoxazol-3-yl)-4-fluoro-5-(5,6,7,8-tetrahydropyrido[3,4-d]pyrimidin-4-yloxy)-1H-indole-1-carboxamide;

5-(6,7-dihydro-5H-pyrrolo[3,4-d]pyrimidin-4-yloxy)-4-fluoro-N-(2-fluoro-3-(trifluoromethyl)phenyl)-1H-indole-1-carboxamide;

N-(5-tert-butylisoxazol-3-yl)-5-(6-methyl-6,7-dihydro-5H-pyrrolo[3,4-d]pyrimidin-4-yloxy)-1H-indole-1-carboxamide;

4-fluoro-5-(6-(hydroxymethyl)pyrimidin-4-yloxy)-N-(3-(trifluoromethyl)phenyl)-1H-indole-1-carboxamide;

N-(2-fluoro-3-(trifluoromethyl)phenyl)-5-(6-(methylsulfonylmethyl)pyrimidin-4-yloxy)-1H-indole-1-carboxamide;

N-(5-cyclopropylisoxazol-3-yl)-5-(6,7-dihydro-5H-pyrrolo[3,4-d]pyrimidin-4-yloxy)-1H-indole-1-carboxamide;

N-(3-isopropyl-1H-pyrazol-5-yl)-5-(6-methyl-5,6,7,8-tetrahydropyrido[3,4-d]pyrimidin-4-yloxy)-1H-indole-1-carboxamide;

N-(3-cyclopropyl-1H-pyrazol-5-yl)-5-(6-methyl-5,6,7,8-tetrahydropyrido[3,4-d]pyrimidin-4-yloxy)-1H-indole-1-carboxamide;

(S)—N-(5-cyclopropylisoxazol-3-yl)-5-(6-methyl-5,6,7,8-tetrahydropyrido[3,4-d]pyrimidin-4-yloxy)-1H-indole-1-carboxamide;

5-(6,7-dihydro-5H-pyrrolo[3,4-d]pyrimidin-4-yloxy)-N-(5-(1-(trifluoromethyl)cyclopropyl)isoxazol-3-yl)-1H-indole-1-carboxamide;

N-(5-cyclopropyl-4-methylisoxazol-3-yl)-5-(6,7-dihydro-5H-pyrrolo[3,4-d]pyrimidin-4-yloxy)-1H-indole-1-carboxamide;

5-(5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

5-(6-methyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

5-(6-((2H-tetrazol-2-yl)methyl)pyrimidin-4-yloxy)-N-(5-cyclopropylisoxazol-3-yl)-1H-indole-1-carboxamide;

N-(5-isopropylisoxazol-3-yl)-5-(6-((methylamino)methyl)pyrimidin-4-yloxy)-1H-indole-1-carboxamide;

(S)—N-(3-isopropyl-1H-pyrazol-5-yl)-5-(6-methyl-5,6,7,8-tetrahydropyrido[3,4-d]pyrimidin-4-yloxy)-1H-indole-1-carboxamide;

N-(1-methyl-5-(1-methylcyclopropyl)-1H-pyrazol-3-yl)-5-(5,6,7,8-tetrahydropyrido[3,4-d]pyrimidin-4-yloxy)-1H-indole-1-carboxamide;

5-(6-((2H-tetrazol-2-yl)methyl)pyrimidin-4-yloxy)-N-(5-isopropylisoxazol-3-yl)-1H-indole-1-carboxamide;

5-(6-((methyl amino)methyl)pyrimidin-4-yloxy)-N-(5-(1-methylcyclopropyl)isoxazol-3-yl)-1H-indole-1-carboxamide;

(S)—N-(5-cyclopropylisoxazol-3-yl)-5-(7-ethanoyl-6-methyl-5,6,7,8-tetrahydropyrido[3,4-d]pyrimidin-4-yloxy)-1H-indole-1-carboxamide;

(S)—N-(5-cyclopropylisoxazol-3-yl)-5-(7-ethyl-6-methyl-5,6,7,8-tetrahydropyrido[3,4-d]pyrimidin-4-yloxy)-1H-indole-1-carboxamide;

N-(5-cyclopropylisoxazol-3-yl)-5-(7-ethanoyl-5,6,7,8-tetrahydropyrido[3,4-d]pyrimidin-4-yloxy)-1H-indole-1-carboxamide 5-(6-((2H-tetrazol-2-yl)methyl)pyrimidin-4-yloxy)-N-(5-(1-methyl cyclopropyl)isoxazol-3-yl)-1H-indole-1-carboxamide;

(S)-5-(7-ethyl-6-methyl-5,6,7,8-tetrahydropyrido[3,4-d]pyrimidin-4-yloxy)-N-(3-(1-methylcyclopropyl)-1H-pyrazol-5-yl)-1H-indole-1-carboxamide;

(S)-5-(6-methyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide (S)—N-(5-cyclopropylisoxazol-3-yl)-5-(6-methyl-7-(methylsulfonyl)-5,6,7,8-tetrahydropyrido[3,4-d]pyrimidin-4-yloxy)-1H-indole-1-carboxamide;

5-(5,7-dihydrothieno[3,4-d]pyrimidin-4-yloxy)-N-(3-(trifluoromethyl)phenyl)-1H-indole-1-carboxamide;

5-(5,7-dihydrothieno[3,4-d]pyrimidin-4-yloxy)-N-(5-(1-methylcyclopropyl)isoxazol-3-yl)-1H-indole-1-carboxamide;

(S)-5-(7-ethanoyl-6-methyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

(S)-5-(7-ethyl-6-methyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

4-chloro-5-(6,7-dihydro-5H-pyrrolo[3,4-d]pyrimidin-4-yloxy)-N-(5-isopropylisoxazol-3-yl)-1H-indole-1-carboxamide;

(S)—N-(4,4-dimethyl-5,6-dihydro-4H-pyrrolo[1,2-b]pyrazol-2-yl)-5-(6-methyl-5,6,7,8-tetrahydropyrido[3,4-d]pyrimidin-4-yloxy)-1H-indole-1-carboxamide;

5-(6,7-dihydro-5H-pyrrolo[3,4-d]pyrimidin-4-yloxy)-N-(4-methyl-5-(1-methylcyclopropyl)isoxazol-3-yl)-1H-indole-1-carboxamide;

N-(5-tert-butyl-4-methylisoxazol-3-yl)-5-(6,7-dihydro-5H-pyrrolo[3,4-d]pyrimidin-4-yloxy)-1H-indole-1-carboxamide;

5-(6,7-dihydro-5H-pyrrolo[3,4-d]pyrimidin-4-yloxy)-N-(5-isopropyl-4-methylisoxazol-3-yl)-1H-indole-1-carboxamide;

N-(5-cyclopropylisoxazol-3-yl)-5-(6,7,8,9-tetrahydro-5H-pyrimido[4,5-c]azepin-4-yloxy)-1H-indole-1-carboxamide;

(S)-5-(6-methyl-5,6,7,8-tetrahydropyrido[3,4-d]pyrimidin-4-yloxy)-N-(1-methyl-5-(1-methylcyclopropyl)-1H-pyrazol-3-yl)-1H-indole-1-carboxamide;

(S)-5-(6-methyl-5,6,7,8-tetrahydropyrido[3,4-d]pyrimidin-4-yloxy)-N-(5-(4,4,4-trifluoro-2-methylbutan-2-yl)isoxazol-3-yl)-1H-indole-1-carboxamide;

5-(6,7,8,9-tetrahydro-5H-pyrimido[4,5-c]azepin-4-yloxy)-N-(5-(1-(trifluoromethyl)cyclopropyl)isoxazol-3-yl)-1H-indole-1-carboxamide;

N-(4-chloro-5-(1-methylcyclopropyl)isoxazol-3-yl)-5-(6,7-dihydro-5H-pyrrolo[3,4-d]pyrimidin-4-yloxy)-1H-indole-1-carboxamide;

(S)-5-(7-(cyclopropylmethyl)-6-methyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

N-(5-tert-butylisoxazol-3-yl)-5-(6,7,8,9-tetrahydro-5H-pyrimido[4,5-c]azepin-4-yloxy)-1H-indole-1-carboxamide;

5-(6-ethanoyl-6,7-dihydro-5H-pyrrolo[3,4-d]pyrimidin-4-yloxy)-N-(2-fluoro-3-(trifluoromethyl)phenyl)-1H-indole-1-carboxamide;

5-(6-ethanoyl-6,7-dihydro-5H-pyrrolo[3,4-d]pyrimidin-4-yloxy)-N-(5-(1-methylcyclopropyl)isoxazol-3-yl)-1H-indole-1-carboxamide;

5-(6-ethanoyl-6,7-dihydro-5H-pyrrolo[3,4-d]pyrimidin-4-yloxy)-N-(5-isopropylisoxazol-3-yl)-1H-indole-1-carboxamide;

N-(5-cyclopropylisoxazol-3-yl)-5-(6-ethanoyl-6,7-dihydro-5H-pyrrolo[3,4-d]pyrimidin-4-yloxy)-1H-indole-1-carboxamide;

5-(6,7-dihydro-5H-pyrrolo[3,4-d]pyrimidin-4-yloxy)-N-(1-isopropyl-5-methyl-1H-pyrazol-3-yl)-1H-indole-1-carboxamide;

(S)-5-(7-(cyclopropanecarbonyl)-6-methyl-5,6,7,8-tetrahydropyrido[3,4-d]pyrimidin-4-yloxy)-N-(5-cyclopropylisoxazol-3-yl)-1H-indole-1-carboxamide;

(S)—N-(5-cyclopropylisoxazol-3-yl)-5-(6,7-dimethyl-5,6,7,8-tetrahydropyrido[3,4-d]pyrimidin-4-yloxy)-1H-indole-1-carboxamide;

(S)-5-(6-methyl-7-(2-methylpropanoyl)-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide (S)-5-(6-methyl-7-(3-methylbutanoyl)-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

5-(5,7-dihydrothieno[3,4-d]pyrimidin-4-yloxy)-N-(5-(1-(trifluoromethyl)cyclopropyl)isoxazol-3-yl)-1H-indole-1-carboxamide;

5-(5,7-dihydrothieno[3,4-d]pyrimidin-4-yloxy)-N-(2-fluoro-3-(trifluoromethyl)phenyl)-1H-indole-1-carboxamide;

N-(4,4-dimethyl-5,6-dihydro-4H-pyrrolo[1,2-b]pyrazol-2-yl)-5-(6-(methylsulfonylmethyl)pyrimidin-4-yloxy)-1H-indole-1-carboxamide;

5-(6-(cyclopropanecarbonyl)-6,7-dihydro-5H-pyrrolo[3,4-d]pyrimidin-4-yloxy)-N-(5-(1-(trifluoromethyl)cyclopropyl)isoxazol-3-yl)-1H-indole-1-carboxamide;

5-(6-(2-methylpropanoyl)-6,7-dihydro-5H-pyrrolo[3,4-d]pyrimidin-4-yloxy)-N-(5-(1-(trifluoromethyl)cyclopropyl)isoxazol-3-yl)-1H-indole-1-carboxamide;

N-(4,4-dimethyl-5,6-dihydro-4H-pyrrolo[1,2-b]pyrazol-2-yl)-5-(6,7,8,9-tetrahydro-5H-pyrimido[4,5-c]azepin-4-yloxy)-1H-indole-1-carboxamide;

5-(6-((methylamino)methyl)pyrimidin-4-yloxy)-N-(5-(1-methylcyclopropyl)-1H-pyrazol-3-yl)-1H-indole-1-carboxamide;

5-(6,7-dihydro-5H-pyrrolo[3,4-d]pyrimidin-4-yloxy)-N-(5-isopropylisoxazol-3-yl)-4-methyl-1H-indole-1-carboxamide;

N-(5-isopropyl-1H-pyrazol-3-yl)-5-(6-((methylamino)methyl)pyrimidin-4-yloxy)-1H-indole-1-carboxamide;

(S)—N-(5-cyclopropylisoxazol-3-yl)-5-(7-(2-hydroxyethyl)-6-methyl-5,6,7,8-tetrahydropyrido[3,4-d]pyrimidin-4-yloxy)-1H-indole-1-carboxamide;

N-(5-cyclopropylisoxazol-3-yl)-5-(6,7-dihydro-5H-pyrrolo[3,4-d]pyrimidin-4-yloxy)-4-methyl-1H-indole-1-carboxamide;

5-(6-((methyl amino)methyl)pyrimidin-4-yloxy)-N-(5-(1-(trifluoromethyl)cyclopropyl)isoxazol-3-yl)-1H-indole-1-carboxamide;

N-(1-isopropyl-5-methyl-1H-pyrazol-3-yl)-5-(6-((methylamino)methyl)pyrimidin-4-yloxy)-1H-indole-1-carboxamide;

(S)—N-(5-cyclopropylisoxazol-3-yl)-5-(6-methyl-7-(2-(methylamino)-2-oxoethyl)-5,6,7,8-tetrahydropyrido[3,4-d]pyrimidin-4-yloxy)-1H-indole-1-carboxamide;

(S)—N-(5-cyclopropylisoxazol-3-yl)-5-(7-isopropyl-6-methyl-5,6,7,8-tetrahydropyrido[3,4-d]pyrimidin-4-yloxy)-1H-indole-1-carboxamide;

(S)—N-(5-cyclopropylisoxazol-3-yl)-5-(6-methyl-7-propyl-5,6,7,8-tetrahydropyrido[3,4-d]pyrimidin-4-yloxy)-1H-indole-1-carboxamide;

N-(1-tert-butyl-1H-pyrazol-3-yl)-5-(5,6,7,8-tetrahydropyrido[3,4-d]pyrimidin-4-yloxy)-1H-indole-1-carboxamide;

5-(6-(cyclopropanecarbonyl)-6,7-dihydro-5H-pyrrolo[3,4-d]pyrimidin-4-yloxy)-N-(5-isopropylisoxazol-3-yl)-1H-indole-1-carboxamide;

N-(5-isopropylisoxazol-3-yl)-5-(6-(2-methylpropanoyl)-6,7-dihydro-5H-pyrrolo[3,4-d]pyrimidin-4-yloxy)-1H-indole-1-carboxamide;

5-(6-(cyclopropanecarbonyl)-6,7-dihydro-5H-pyrrolo[3,4-d]pyrimidin-4-yloxy)-N-(5-cyclopropylisoxazol-3-yl)-1H-indole-1-carboxamide;

N-(5-cyclopropylisoxazol-3-yl)-5-(6-(2-methylpropanoyl)-6,7-dihydro-5H-pyrrolo[3,4-d]pyrimidin-4-yloxy)-1H-indole-1-carboxamide;

5-(6-(cyclopropanecarbonyl)-6,7-dihydro-5H-pyrrolo[3,4-d]pyrimidin-4-yloxy)-N-(5-(1-methylcyclopropyl)isoxazol-3-yl)-1H-indole-1-carboxamide;

N-(5-(1-methylcyclopropyl)isoxazol-3-yl)-5-(6-(2-methylpropanoyl)-6,7-dihydro-5H-pyrrolo[3,4-d]pyrimidin-4-yloxy)-1H-indole-1-carboxamide;

(S)—N-(5-cyclopropylisoxazol-3-yl)-5-(6-methyl-7-(2-methylpropanoyl)-5,6,7,8-tetrahydropyrido[3,4-d]pyrimidin-4-yloxy)-1H-indole-1-carboxamide;

(S)—N-(5-cyclopropylisoxazol-3-yl)-5-(6-methyl-7-(3-methylbutanoyl)-5,6,7,8-tetrahydropyrido[3,4-d]pyrimidin-4-yloxy)-1H-indole-1-carboxamide;

(S)-4-(1-(5-cyclopropylisoxazol-3-ylcarbamoyl)-1H-indol-5-yloxy)-N-ethyl-6-methyl-5,6-dihydropyrido[3,4-d]pyrimidine-7(8H)-carboxamide;

(S)—N-(5,6-dihydro-4H-pyrrolo[1,2-b]pyrazol-2-yl)-5-(7-ethanoyl-6-methyl-5,6,7,8-tetrahydropyrido[3,4-d]pyrimidin-4-yloxy)-1H-indole-1-carboxamide;

(R)—N-(5-cyclopropylisoxazol-3-yl)-5-(6-methyl-5,6,7,8-tetrahydropyrido[3,4-d]pyrimidin-4-yloxy)-1H-indole-1-carboxamide;

(S)-5-(7-butyl-6-methyl-5,6,7,8-tetrahydropyrido[3,4-d]pyrimidin-4-yloxy)-N-(5-cyclopropylisoxazol-3-yl)-1H-indole-1-carboxamide;

(S)—N-(5-cyclopropylisoxazol-3-yl)-5-(7-isopentyl-6-methyl-5,6,7,8-tetrahydropyrido[3,4-d]pyrimidin-4-yloxy)-1H-indole-1-carboxamide;

(R)—N-(5-cyclopropylisoxazol-3-yl)-5-(7-ethanoyl-6-methyl-5,6,7,8-tetrahydropyrido[3,4-d]pyrimidin-4-yloxy)-1H-indole-1-carboxamide;

(S)-5-(6-methyl-7-propyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

(S)—N-(5-cyclopropylisoxazol-3-yl)-5-(6-methyl-7-propanoyl-5,6,7,8-tetrahydropyrido[3,4-d]pyrimidin-4-yloxy)-1H-indole-1-carboxamide;

(S)-5-(7-butanoyl-6-methyl-5,6,7,8-tetrahydropyrido[3,4-d]pyrimidin-4-yloxy)-N-(5-cyclopropylisoxazol-3-yl)-1H-indole-1-carboxamide;

(S)-5-(6,7-dimethyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

5-(8-ethyl-6,7,8,9-tetrahydro-5H-pyrimido[4,5-c]azepin-4-yloxy)-N-(5-(1-(trifluoromethyl)cyclopropyl)isoxazol-3-yl)-1H-indole-1-carboxamide;1

(S)-5-(7-ethanoyl-6-methyl-5,6,7,8-tetrahydropyrido[3,4-d]pyrimidin-4-yloxy)-N-(5-isopropylisoxazol-3-yl)-1H-indole-1-carboxamide;

(S)-4-methyl-5-(6-methyl-5,6,7,8-tetrahydropyrido[3,4-d]pyrimidin-4-yloxy)-N-(5-(1-(trifluoromethyl)cyclopropyl)isoxazol-3-yl)-1H-indole-1-carboxamide;

(S)-5-(7-(cyclobutanecarbonyl)-6-methyl-5,6,7,8-tetrahydropyrido[3,4-d]pyrimidin-4-yloxy)-N-(5-cyclopropylisoxazol-3-yl)-1H-indole-1-carboxamide;

(S)—N-(5-cyclopropylisoxazol-3-yl)-4-methyl-5-(6-methyl-5,6,7,8-tetrahydropyrido[3,4-d]pyrimidin-4-yloxy)-1H-indole-1-carboxamide;

(S)-5-(7-ethanoyl-6-methyl-5,6,7,8-tetrahydropyrido[3,4-d]pyrimidin-4-yloxy)-N-(5-isopropylisoxazol-3-yl)-4-methyl-1H-indole-1-carboxamide;

(S)-5-(7-ethanoyl-6-methyl-5,6,7,8-tetrahydropyrido[3,4-d]pyrimidin-4-yloxy)-4-methyl-N-(5-(1-methylcyclopropyl)isoxazol-3-yl)-1H-indole-1-carboxamide;

(S)-5-(7-ethanoyl-6-methyl-5,6,7,8-tetrahydropyrido[3,4-d]pyrimidin-4-yloxy)-4-methyl-N-(5-(1-(trifluoromethyl)cyclopropyl)isoxazol-3-yl)-1H-indole-1-carboxamide;

(S)-5-(7-ethanoyl-6-methyl-5,6,7,8-tetrahydropyrido[3,4-d]pyrimidin-4-yloxy)-N-(5-methylisoxazol-3-yl)-1H-indole-1-carboxamide;

(S)—N-(5-isopropylisoxazol-3-yl)-4-methyl-5-(6-methyl-5,6,7,8-tetrahydropyrido[3,4-d]pyrimidin-4-yloxy)-1H-indole-1-carboxamide;
(S)-4-methyl-5-(6-methyl-5,6,7,8-tetrahydropyrido[3,4-d]pyrimidin-4-yloxy)-N-(5-(1-methylcyclopropyl)isoxazol-3-yl)-1H-indole-1-carboxamide;
(S)—N-(1-tert-butyl-1H-pyrazol-3-yl)-5-(6-methyl-5,6,7,8-tetrahydropyrido[3,4-d]pyrimidin-4-yloxy)-1H-indole-1-carboxamide;
5-(6-ethanoyl-6,7-dihydro-5H-pyrrolo[3,4-d]pyrimidin-4-yloxy)-4-methyl-N-(5-(1-methylcyclopropyl)isoxazol-3-yl)-1H-indole-1-carboxamide;
(S)-5-(7-ethanoyl-6-methyl-5,6,7,8-tetrahydropyrido[3,4-d]pyrimidin-4-yloxy)-N-(3-(trifluoromethyl)phenyl)-1H-indole-1-carboxamide;
(S)—N-(5-cyclopropylisoxazol-3-yl)-5-(7-ethanoyl-6-methyl-5,6,7,8-tetrahydropyrido[3,4-d]pyrimidin-4-yloxy)-4-methyl-1H-indole-1-carboxamide;
5-(6-ethanoyl-6,7-dihydro-5H-pyrrolo[3,4-d]pyrimidin-4-yloxy)-4-methyl-N-(5-(1-(trifluoromethyl)cyclopropyl)isoxazol-3-yl)-1H-indole-1-carboxamide;
(S)—N-(1-tert-butyl-1H-pyrazol-3-yl)-5-(7-ethanoyl-6-methyl-5,6,7,8-tetrahydropyrido[3,4-d]pyrimidin-4-yloxy)-1H-indole-1-carboxamide;
N-(5-cyclopropyl-1H-pyrazol-3-yl)-5-(6-((methylamino)methyl)pyrimidin-4-yloxy)-1H-indole-1-carboxamide;
N-(5-cyclopropylisoxazol-3-yl)-5-(6-ethanoyl-6,7-dihydro-5H-pyrrolo[3,4-d]pyrimidin-4-yloxy)-4-methyl-1H-indole-1-carboxamide;
N-(1-tert-butyl-1H-pyrazol-3-yl)-5-(6,7-dihydro-5H-pyrrolo[3,4-d]pyrimidin-4-yloxy)-1H-indole-1-carboxamide;
N-(1-tert-butyl-1H-pyrazol-3-yl)-5-(6-((methylamino)methyl)pyrimidin-4-yloxy)-1H-indole-1-carboxamide;
5-(6-((ethyl amino)methyl)pyrimidin-4-yloxy)-N-(5-isopropyl-1H-pyrazol-3-yl)-1H-indole-1-carboxamide;
5-(6-(2-(dimethylamino)ethyl)pyrimidin-4-yloxy)-N-(5-isopropyl-1H-pyrazol-3-yl)-1H-indole-1-carboxamide;
N-(5-cyclopropyl-1-methyl-1H-pyrazol-3-yl)-5-(6-((methylamino)methyl)pyrimidin-4-yloxy)-1H-indole-1-carboxamide;
N-(1-methyl-5-(trifluoromethyl)-1H-pyrazol-3-yl)-5-(6-((methylamino)methyl)pyrimidin-4-yloxy)-1H-indole-1-carboxamide N-(5-methyl-1-(2,2,2-trifluoroethyl)-1H-pyrazol-3-yl)-5-(6-((methylamino)methyl)pyrimidin-4-yloxy)-1H-indole-1-carboxamide;
5-(6,7-dihydro-5H-pyrrolo[3,4-d]pyrimidin-4-yloxy)-N-(1-methyl-5-(trifluoromethyl)-1H-pyrazol-3-yl)-1H-indole-1-carboxamide;
(S)-5-(6-methyl-5,6,7,8-tetrahydropyrido[3,4-d]pyrimidin-4-yloxy)-N-(1-methyl-5-(trifluoromethyl)-1H-pyrazol-3-yl)-1H-indole-1-carboxamide;
5-(5,7-dihydrothieno[3,4-d]pyrimidin-4-yloxy)-N-(1-methyl-5-(trifluoromethyl)-1H-pyrazol-3-yl)-1H-indole-1-carboxamide;
(S)-5-(7-ethanoyl-6-methyl-5,6,7,8-tetrahydropyrido[3,4-d]pyrimidin-4-yloxy)-N-(1-ethyl-1H-pyrazol-3-yl)-1H-indole-1-carboxamide;
(S)-5-(7-ethanoyl-6-methyl-5,6,7,8-tetrahydropyrido[3,4-d]pyrimidin-4-yloxy)-N-(1-ethyl-5-methyl-1H-pyrazol-3-yl)-1H-indole-1-carboxamide;
(S)—N-(1-cyclopropyl-5-methyl-1H-pyrazol-3-yl)-5-(7-ethanoyl-6-methyl-5,6,7,8-tetrahydropyrido[3,4-d]pyrimidin-4-yloxy)-1H-indole-1-carboxamide;
(S)—N-(1-cyclopropyl-1H-pyrazol-3-yl)-5-(7-ethanoyl-6-methyl-5,6,7,8-tetrahydropyrido[3,4-d]pyrimidin-4-yloxy)-1H-indole-1-carboxamide;
(S)-5-(7-ethanoyl-6-methyl-5,6,7,8-tetrahydropyrido[3,4-d]pyrimidin-4-yloxy)-N-(1-isopropyl-5-methyl-1H-pyrazol-3-yl)-1H-indole-1-carboxamide;
N-(5-cyclopropyl-1-methyl-1H-pyrazol-3-yl)-5-(6-ethanoyl-6,7-dihydro-5H-pyrrolo[3,4-d]pyrimidin-4-yloxy)-1H-indole-1-carboxamide;
5-(6-ethanoyl-6,7-dihydro-5H-pyrrolo[3,4-d]pyrimidin-4-yloxy)-N-(1-methyl-5-(trifluoromethyl)-1H-pyrazol-3-yl)-1H-indole-1-carboxamide;
(S)—N-(5-cyclopropyl-1-methyl-1H-pyrazol-3-yl)-5-(7-ethanoyl-6-methyl-5,6,7,8-tetrahydropyrido[3,4-d]pyrimidin-4-yloxy)-1H-indole-1-carboxamide;
(S)-5-(7-ethanoyl-6-methyl-5,6,7,8-tetrahydropyrido[3,4-d]pyrimidin-4-yloxy)-N-(1-methyl-5-(trifluoromethyl)-1H-pyrazol-3-yl)-1H-indole-1-carboxamide;
(S)-5-(7-ethanoyl-6-methyl-5,6,7,8-tetrahydropyrido[3,4-d]pyrimidin-4-yloxy)-N-(5-methyl-1-(2,2,2-trifluoroethyl)-1H-pyrazol-3-yl)-1H-indole-1-carboxamide;
N-(1-cyclopropyl-5-methyl-1H-pyrazol-3-yl)-5-(6,7-dihydro-5H-pyrrolo[3,4-d]pyrimidin-4-yloxy)-1H-indole-1-carboxamide;
(S)—N-(1-tert-butyl-5-methyl-1H-pyrazol-3-yl)-5-(6-methyl-5,6,7,8-tetrahydropyrido[3,4-d]pyrimidin-4-yloxy)-1H-indole-1-carboxamide;
N-(5-cyclopropyl-1H-pyrazol-3-yl)-4-methyl-5-(6-((methylamino)methyl)pyrimidin-4-yloxy)-1H-indole-1-carboxamide;
N-(5-cyclopropyl-1-methyl-1H-pyrazol-3-yl)-4-methyl-5-(6-((methylamino)methyl)pyrimidin-4-yloxy)-1H-indole-1-carboxamide;
4-methyl-N-(1-methyl-5-(trifluoromethyl)-1H-pyrazol-3-yl)-5-(6-((methylamino)methyl)pyrimidin-4-yloxy)-1H-indole-1-carboxamide;
(S)—N-(1,5-dimethyl-1H-pyrazol-3-yl)-5-(7-ethanoyl-6-methyl-5,6,7,8-tetrahydropyrido[3,4-d]pyrimidin-4-yloxy)-1H-indole-1-carboxamide;
(S)—N-(1-tert-butyl-5-methyl-1H-pyrazol-3-yl)-5-(7-ethanoyl-6-methyl-5,6,7,8-tetrahydropyrido[3,4-d]pyrimidin-4-yloxy)-1H-indole-1-carboxamide;
5-(6,7-dihydro-5H-pyrrolo[3,4-d]pyrimidin-4-yloxy)-N-(1-ethyl-5-methyl-1H-pyrazol-3-yl)-1H-indole-1-carboxamide;
N-(1-ethyl-5-methyl-1H-pyrazol-3-yl)-5-(6-((methylamino)methyl)pyrimidin-4-yloxy)-1H-indole-1-carboxamide;
N-(1-tert-butyl-5-methyl-1H-pyrazol-3-yl)-5-(6-((methylamino)methyl)pyrimidin-4-yloxy)-1H-indole-1-carboxamide;
N-(5-isopropyl-1-methyl-1H-pyrazol-3-yl)-5-(6-((methylamino)methyl)pyrimidin-4-yloxy)-1H-indole-1-carboxamide;
N-(1-ethyl-5-(trifluoromethyl)-1H-pyrazol-3-yl)-5-(6-((methylamino)methyl)pyrimidin-4-yloxy)-1H-indole-1-carboxamide;
N-(5-tert-butyl-1-methyl-1H-pyrazol-3-yl)-5-(6-((methylamino)methyl)pyrimidin-4-yloxy)-1H-indole-1-carboxamide;
(S)—N-(1-tert-butyl-1H-pyrazol-3-yl)-4-methyl-5-(6-methyl-5,6,7,8-tetrahydropyrido[3,4-d]pyrimidin-4-yloxy)-1H-indole-1-carboxamide;
N-(5-cyclopropyl-1-ethyl-1H-pyrazol-3-yl)-5-(6-((methylamino)methyl)pyrimidin-4-yloxy)-1H-indole-1-carboxamide;
(S)—N-(1-ethyl-5-(trifluoromethyl)-1H-pyrazol-3-yl)-4-methyl-5-(6-methyl-5,6,7,8-tetrahydropyrido[3,4-d]pyrimidin-4-yloxy)-1H-indole-1-carboxamide;

(S)—N-(1-ethyl-5-(trifluoromethyl)-1H-pyrazol-3-yl)-5-(6-methyl-5,6,7,8-tetrahydropyrido[3,4-d]pyrimidin-4-yloxy)-1H-indole-1-carboxamide;

(S)-5-(7-ethanoyl-6-methyl-5,6,7,8-tetrahydropyrido[3,4-d]pyrimidin-4-yloxy)-N-(1-ethyl-5-(trifluoromethyl)-1H-pyrazol-3-yl)-1H-indole-1-carboxamide;

(S)-5-(7-(cyclopropanecarbonyl)-6-methyl-5,6,7,8-tetrahydropyrido[3,4-d]pyrimidin-4-yloxy)-N-(5-cyclopropylisoxazol-3-yl)-4-methyl-1H-indole-1-carboxamide;

(S)-4-methyl-5-(6-methyl-5,6,7,8-tetrahydropyrido[3,4-d]pyrimidin-4-yloxy)-N-(1-methyl-5-(trifluoromethyl)-1H-pyrazol-3-yl)-1H-indole-1-carboxamide;

(S)-ethyl 4-(1-(5-cyclopropylisoxazol-3-ylcarbamoyl)-4-methyl-1H-indol-5-yloxy)-6-methyl-5,6-dihydropyrido[3,4-d]pyrimidine-7(8H)-carboxylate;

N-(1-methyl-5-(1-methylcyclopropyl)-1H-pyrazol-3-yl)-5-(6-((methylamino)methyl)pyrimidin-4-yloxy)-1H-indole-1-carboxamide;

(S)—N-(5-cyclopropylisoxazol-3-yl)-4-methyl-5-(6-methyl-7-propanoyl-5,6,7,8-tetrahydropyrido[3,4-d]pyrimidin-4-yloxy)-1H-indole-1-carboxamide;

(S)—S-(7-ethanoyl-6-methyl-5,6,7,8-tetrahydropyrido[3,4-d]pyrimidin-4-yloxy)-4-methyl-N-(1-methyl-5-(trifluoromethyl)-1H-pyrazol-3-yl)-1H-indole-1-carboxamide;

(S)—S-(7-ethanoyl-6-methyl-5,6,7,8-tetrahydropyrido[3,4-d]pyrimidin-4-yloxy)-N-(1-ethyl-5-(trifluoromethyl)-1H-pyrazol-3-yl)-4-methyl-1H-indole-1-carboxamide;

N-(5-cyclopropyl-1-methyl-1H-pyrazol-3-yl)-5-(2-((methylamino)methyl)pyridin-4-yloxy)-1H-indole-1-carboxamide;

N-(1-cyclopropyl-5-methyl-1H-pyrazol-3-yl)-5-(6-((methylamino)methyl)pyrimidin-4-yloxy)-1H-indole-1-carboxamide;

N-(1,5-dicyclopropyl-1H-pyrazol-3-yl)-5-(6-((methylamino)methyl)pyrimidin-4-yloxy)-1H-indole-1-carboxamide;

N-(1-methyl-5-(trifluoromethyl)-1H-pyrazol-3-yl)-5-(2-((methylamino)methyl)pyridin-4-yloxy)-1H-indole-1-carboxamide;

(S)—S-(7-(cyclopropanecarbonyl)-6-methyl-5,6,7,8-tetrahydropyrido[3,4-d]pyrimidin-4-yloxy)-N-(1-methyl-5-(trifluoromethyl)-1H-pyrazol-3-yl)-1H-indole-1-carboxamide;

N-(5-cyclopropyl-1-isopropyl-1H-pyrazol-3-yl)-5-(6-((methylamino)methyl)pyrimidin-4-yloxy)-1H-indole-1-carboxamide;

(S)—N-(5-cyclopropyl-1-isopropyl-1H-pyrazol-3-yl)-5-(6-methyl-5,6,7,8-tetrahydropyrido[3,4-d]pyrimidin-4-yloxy)-1H-indole-1-carboxamide;

(S)—N-(5-cyclopropyl-1-isopropyl-1H-pyrazol-3-yl)-5-(7-ethanoyl-6-methyl-5,6,7,8-tetrahydropyrido[3,4-d]pyrimidin-4-yloxy)-1H-indole-1-carboxamide;

N-(1-cyclopropyl-5-ethyl-1H-pyrazol-3-yl)-5-(6-((methylamino)methyl)pyrimidin-4-yloxy)-1H-indole-1-carboxamide;

(S)-ethyl 6-methyl-4-(1-(5-(1-(trifluoromethyl)cyclopropyl)isoxazol-3-ylcarbamoyl)-1H-indol-5-yloxy)-5,6-dihydropyrido[3,4-d]pyrimidine-7(8H)-carboxylate;

(S)-ethyl 4-(1-(5-cyclopropylisoxazol-3-ylcarbamoyl)-1H-indol-5-yloxy)-6-methyl-5,6-dihydropyrido[3,4-d]pyrimidine-7(8H)-carboxylate;

(S)-methyl 6-methyl-4-(1-(5-(1-(trifluoromethyl)cyclopropyl)isoxazol-3-ylcarbamoyl)-1H-indol-5-yloxy)-5,6-dihydropyrido[3,4-d]pyrimidine-7(8H)-carboxylate;

N-(1-methyl-5-(trifluoromethyl)-1H-pyrazol-3-yl)-5-(6-(methylsulfonylmethyl)pyrimidin-4-yloxy)-1H-indole-1-carboxamide;

5-(6-(aminomethyl)pyrimidin-4-yloxy)-N-(1-methyl-5-(trifluoromethyl)-1H-pyrazol-3-yl)-1H-indole-1-carboxamide;

(S)—N-(1-cyclopropyl-5-ethyl-1H-pyrazol-3-yl)-5-(7-ethanoyl-6-methyl-5,6,7,8-tetrahydropyrido[3,4-d]pyrimidin-4-yloxy)-1H-indole-1-carboxamide;

(S)—N-(1,5-dicyclopropyl-1H-pyrazol-3-yl)-5-(6-methyl-5,6,7,8-tetrahydropyrido[3,4-d]pyrimidin-4-yloxy)-1H-indole-1-carboxamide 5-(6-(aminomethyl)pyrimidin-4-yloxy)-N-(5-cyclopropyl-1-methyl-1H-pyrazol-3-yl)-1H-indole-1-carboxamide;

N-(5-cyclopropyl-1-methyl-1H-pyrazol-3-yl)-5-(6-((ethylamino)methyl)pyrimidin-4-yloxy)-1H-indole-1-carboxamide; and (S)—N-(1,5-dicyclopropyl-1H-pyrazol-3-yl)-5-(7-ethanoyl-6-methyl-5,6,7,8-tetrahydropyrido[3,4-d]pyrimidin-4-yloxy)-1H-indole-1-carboxamide.

6. An ophthalmic composition as in claim 1 wherein the 1H-indole-1-carboxamide is N-(1-methyl-5-(trifluoromethyl)-1H-pyrazol-3-yl)-5-((6-((methylamino)methyl)pyrimidin-4-yl)oxy)-1H-indole-1-carboxamide.

7. An ophthalmic composition as in claim 1 wherein the 1H-indole-1-carboxamide is in the composition at a concentration that is greater than 1.8 w/v % but less than 3.3 w/v %.

8. An ophthalmic composition as in claim 1 wherein the osmolality of the composition is in the range 240 to 360 mOsm/kg.

9. An ophthalmic composition as in claim 1 wherein the HEC is in the composition at a concentration that is greater than 0.25 w/v % but less than 0.7 w/v % and wherein the weight average molecular weight of the HEC is from 250,000 to 1,500,000.

10. An ophthalmic composition as in claim 1 wherein the charged and/or salt form CMC is NaCMC.

11. An ophthalmic composition as in claim 1 wherein the concentration of suspending agent in the composition is at least 0.1 w/v % but less than 0.5 w/v %.

12. An ophthalmic composition as in claim 10 wherein the concentration of NaCMC in the composition is at least 0.6 w/v % but no greater than 1.5 w/v %.

13. An ophthalmic composition as in claim 12 wherein the viscosity of the composition is at least 15 cP but no greater than 65 cP.

14. An ophthalmic composition as in claim 1 wherein the composition is disposed within a dispenser configured to deliver the composition to a cornea of an eye.

15. An ophthalmic composition as in claim 14 wherein the dispenser is an eyedropper that dispenses individual drops of the composition to the outer surface of the cornea of the eye.

16. A multi-dose aqueous ophthalmic suspension composition, comprising:

a 1H-indole-1-carboxamide of formula I below:

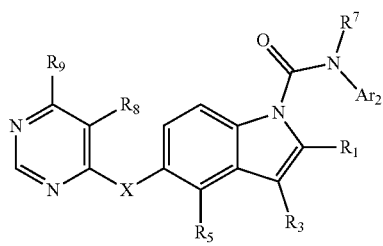

or a pharmaceutically acceptable salt thereof, wherein:

$R_1$ is hydrogen or $C_1$-$C_6$alkyl;
$R_3$ is hydrogen or $C_1$-$C_6$alkyl;
$R_5$ is hydrogen or halogen;
$R_7$ is hydrogen or $C_1$-$C_6$alkyl;
X is O or S;
$R_8$ is selected from the group consisting of hydrogen and $C_1$-$C_4$alkyl;
$R_9$ is selected from the group consisting of $(CR_{11}R_{12})_n NR_{13}R_{14}$, $(CR_{11}R_{12})_n$heterocycle, $(CR_{11}R_{12})_n OR_{15}$, $(CR_{11}R_{12})_n C(O)ER_{13}$, and $(CR_{11}R_{12})_n S(O)_m R_{17}$; or
$R_8$ and $R_9$, taken in combination together with the atoms to which they are attached form a saturated 4-7 membered heterocyclic ring having 1 or 2 ring heteroatoms selected from N, O or S, which heterocyclic ring is substituted with 0, 1, or 2 groups independently selected from the group consisting of $C_1$-$C_6$alkyl, $C_1$-$C_6$haloalkyl, halogen, hydroxy$C_1$-$C_6$alkyl, amino$C_1$-$C_6$alkyl, $C_3$-$C_7$cycloalkyl$C_1$-$C_4$alkyl, heterocycle$C_1$-$C_4$alkyl, $C_1$-$C_6$alkanoyl, mono- and di-$C_1$-$C_6$alkylaminocarbonyl, $C_1$-$C_6$alkoxycarbonyl, and $C_1$-$C_6$alkylsulfonyl;
$Ar_2$ is phenyl, naphthyl, 5 or 6 membered monocyclic heteroaryl, wherein each heteroaryl has 1, 2, or 3 ring heteroatoms selected from N, O or S and wherein the phenyl, naphthyl, or heteroaryl group is unsubstituted or substituted by 1, 2, or 3 groups independently selected from the group consisting of $C_1$-$C_6$alkyl, $C_1$-$C_6$haloalkyl, halo, hydroxyl, $CO_2 C_1$-$C_6$alkyl, phenyl, and $C_3$-$C_7$cycloalkyl;
m is 0, 1, or 2;
n is 1, 2, or 3;
E is 0 or $NR_{18}$;
$R_{11}$, $R_{12}$ and $R_{18}$ are the same or different and are independently selected at each occurrence from the group consisting of hydrogen and $C_1$-$C_4$alkyl; and
$R_{13}$, $R_{14}$, $R_{15}$, $R_{16}$ and $R_{17}$ are independently selected at each occurrence from the group consisting of hydrogen, $C_1$-$C_6$alkyl, $C_3$-$C_6$cycloalkyl, phenyl and heterocycle, each of which is substituted with 0, 1 or 2 groups independently selected from hydroxyl, amino, and mono- and di-$C_1$-$C_6$alkylamino; and
wherein the concentration of 1H-indole-1-carboxamide in the composition is greater than 1.0 w/v % but less than 4.0 w/v %;
an ophthalmic vehicle comprised at least 80 w/v % water, a suspending agent that suspends the 1H-indole-1-carboxamide, sodium carboxymethylcellulose (NaCMC), a preservative, and an ingredient selected from the group consisting of a surfactant, a buffer, a polyol, and an osmolality agent;
wherein the preservative is benzalkonium chloride;
wherein the composition has a pH in the range of 6.4 to 7.6 and an osmolality of 200 to 450 mOsm/kg and wherein the suspending agent is hydroxyethylcellulose (HEC) and wherein the HEC is in the composition at a concentration that is greater than 0.25 w/v % but less than 0.7 w/v % and wherein the weight average molecular weight of the HEC is from 250,000 to 1,500,000 and wherein the NaCMC is in the composition at a concentration that is at least 0.6 w/v % but no greater than 1.5 w/v % and wherein the viscosity of the composition is at least 15 cP but no greater than 65 cP.

17. An ophthalmic composition as in claim 16 wherein the concentration of NaCMC in the composition is at least 0.8 w/v % but no greater than 1.3 w/v %.

18. An ophthalmic composition as in claim 17 wherein the viscosity of the composition is at least 20 cP but no greater than 50 cP.

* * * * *